US011466182B2

(12) United States Patent
Lotti

(10) Patent No.: US 11,466,182 B2
(45) Date of Patent: Oct. 11, 2022

(54) CHARCOAL ADHESIVE COMPOSITION FOR LASHES OR LASH EXTENSIONS

(71) Applicant: Lashify, Inc., Los Angeles, CA (US)

(72) Inventor: Sahara Lotti, Los Angeles, CA (US)

(73) Assignee: Lashify, Inc., North Hollywood, CA (US)

( * ) Notice: Subject to any disclaimer, the term of this patent is extended or adjusted under 35 U.S.C. 154(b) by 0 days.

(21) Appl. No.: 17/034,715

(22) Filed: Sep. 28, 2020

(65) Prior Publication Data

US 2021/0095170 A1    Apr. 1, 2021

Related U.S. Application Data

(60) Provisional application No. 62/908,143, filed on Sep. 30, 2019.

(51) Int. Cl.
| | | |
|---|---|---|
| *C09J 133/08* | (2006.01) | |
| *C09J 133/10* | (2006.01) | |
| *A41G 5/02* | (2006.01) | |
| *C08K 3/04* | (2006.01) | |

(52) U.S. Cl.
CPC .............. *C09J 133/08* (2013.01); *A41G 5/02* (2013.01); *C08K 3/04* (2013.01); *C09J 133/10* (2013.01); *C09J 2203/00* (2013.01); *C09J 2433/00* (2013.01)

(58) Field of Classification Search
CPC .................................................... C09J 133/08
See application file for complete search history.

(56) References Cited

U.S. PATENT DOCUMENTS

| | | | | |
|---|---|---|---|---|
| 6,210,694 | B1* | 4/2001 | Park .................... | A61K 8/9789 |
| | | | | 424/401 |
| 6,270,783 | B1* | 8/2001 | Slavtcheff ........... | A61K 8/0208 |
| | | | | 424/10.1 |
| 2002/0128579 | A1* | 9/2002 | Church .................. | A61F 13/00 |
| | | | | 602/48 |
| 2005/0107547 | A1* | 5/2005 | Ohno ..................... | C08F 2/38 |
| | | | | 525/329.7 |
| 2009/0035246 | A1* | 2/2009 | Do ......................... | A61K 8/895 |
| | | | | 424/70.7 |
| 2011/0243864 | A1 | 10/2011 | Farcet et al. | |
| 2011/0293680 | A1 | 12/2011 | Jo et al. | |
| 2012/0247497 | A1* | 10/2012 | Zhang .................... | C09J 4/00 |
| | | | | 132/201 |

(Continued)

FOREIGN PATENT DOCUMENTS

| | | |
|---|---|---|
| CN | 102421483 A | 4/2012 |
| CN | 106074193 A | 11/2016 |
| CN | 110236984 A | 9/2019 |

(Continued)

OTHER PUBLICATIONS

International Search Report and Written Opinion dated Dec. 8, 2020, on application No. PCT/US2020/053321.

(Continued)

*Primary Examiner* — Daniel H Lee
(74) *Attorney, Agent, or Firm* — Lowenstein Sandler LLP

(57) ABSTRACT

Provided are adhesive compositions that include an acrylate component and a charcoal component. The adhesive compositions are useful for adhering articles, for example, lashes or lash extensions to surfaces such as skin.

13 Claims, 9 Drawing Sheets

(56) References Cited

U.S. PATENT DOCUMENTS

2017/0027844 A1* 2/2017 Okura .................. A61K 8/735
2019/0002703 A1 1/2019 Cho et al.

FOREIGN PATENT DOCUMENTS

| | | |
|---|---|---|
| JP | 20063282264 | 12/1899 |
| JP | 2006022008 A | 1/2006 |
| KR | 101181622 | 1/2006 |
| KR | 20060040877 A | 5/2006 |
| KR | 20190035787 A | 4/2019 |
| WO | 2010046229 A1 | 4/2010 |

OTHER PUBLICATIONS

Search Report for Chinese patent application No. 2019112944863 dated Nov. 24, 2021, one page.

* cited by examiner

CHARCOAL ADHESIVE COMPOSITION FOR LASHES OR LASH EXTENSIONS

CROSS-REFERENCE TO RELATED APPLICATION(S)

This application claims the benefit under 35 U.S.C. § 119(e) of U.S. Provisional Application No. 62/908,143 filed on Sep. 30, 2019, the contents of which are hereby incorporated by reference in their entirety.

FIELD

The present disclosure relates to adhesive compositions for use with beauty articles such as lashes or lash extensions.

BACKGROUND

In recent years, the use of eyelash extensions has increased in popularity. There are various approaches for adhering eyelash extensions, ranging from magnets to different types of adhesives.

SUMMARY

Figure 1:
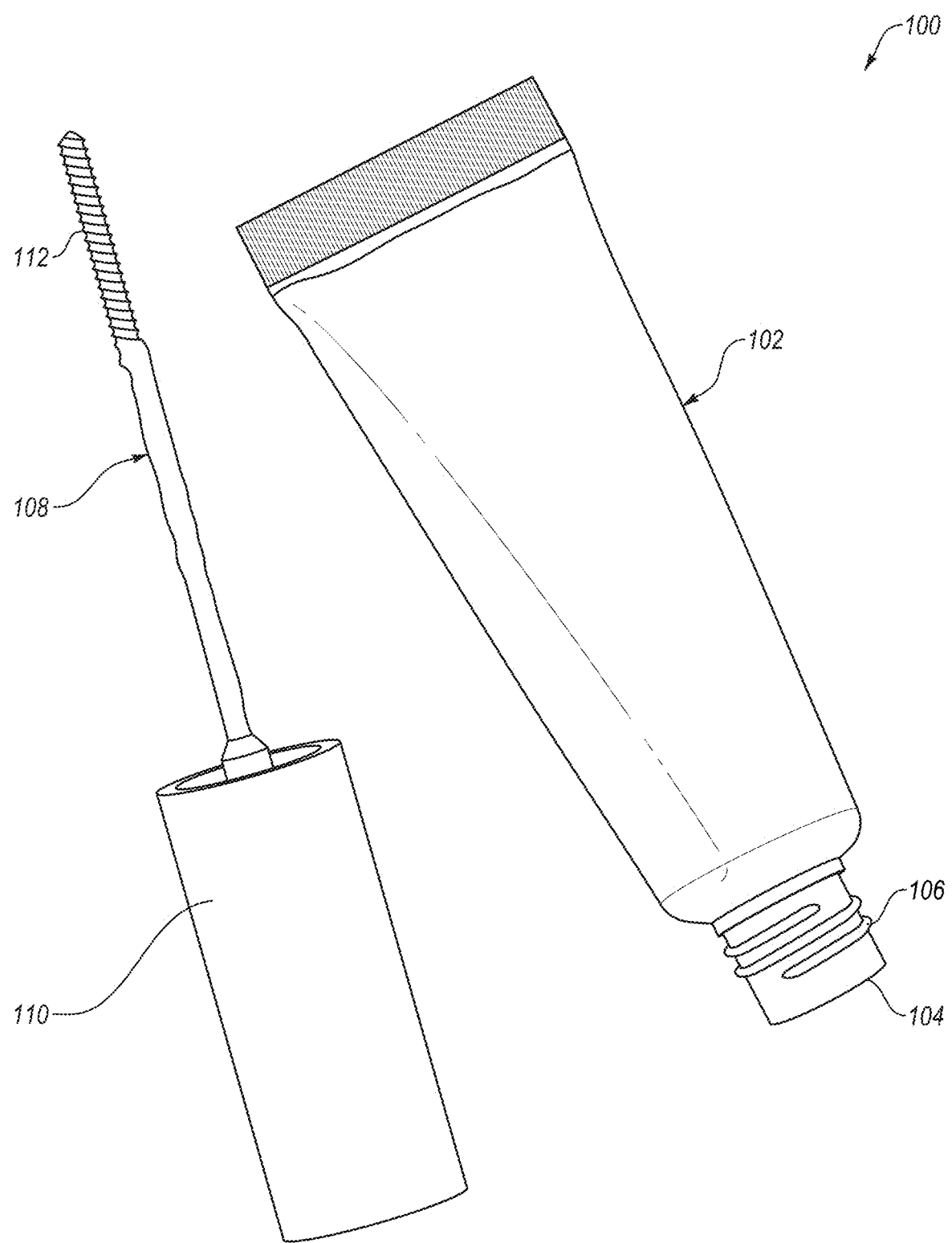
FIG. 1 illustrates an example embodiment of a kit containing an adhesive composition according to some embodiments herein.

According to some embodiments, provided is a glue composition for use in adhering lashes or lash extensions to natural lashes. Such adhesive compositions include charcoal.

In some embodiments, an adhesive composition for adhering lashes or lash extensions to an eye area may include an acrylate component and a charcoal component.

According to some embodiments, provided is an adhesive composition for application of one or more of a beauty article, the adhesive composition comprising: an acrylate component; and a charcoal component. In some embodiments, the acrylate component in an amount of about 10 percent by weight (wt %) to about 90 wt % based on a total weight of the adhesive composition. The acrylate component may comprise acrylates, polyacrylates, acrylamide polymers, alkyl acrylates, (meth)acrylates, acrylic acids, (meth)acrylic acid, acrylamide, (meth)acrylamide polymers, polymethacrylate, polymethylmethacrylate, $C_{1-6}$hydroxyalkyl (meth)acrylates, $C_{1-6}$alkoxy $C_{1-6}$alkyl (meth)acrylates, polyoxyalkylene (meth)acrylates, $C_{1-6}$alkylpolyoxyalkylene (meth)acrylates, $C_{8-22}$alkyl (meth)acrylates, methyl(meth)acrylate, ethyl(meth)acrylate, propyl(meth)acrylate, butyl (meth)acrylate, isobutyl(meth)acrylate, pentyl(meth)acrylate, hexyl(meth)acrylate, 2-hydroxyethyl(meth)acrylate, 2-methoxyethyl(meth)acrylate, polyoxyallcylene (meth)acrylates, polyethyl eneglycol (meth)acrylate, polyethyl eneglycol methyl ether (meth)acrylate, polyethyleneglycol ethyl ether (meth)acrylate, octyl(meth)acrylate, 2-ethylhexyl(meth)acrylate, lauryl(meth)acrylate, stearyl(meth)acrylate, 2-ethylhexyl acrylate, copolymers thereof, quaternary salts thereof, ethylhexyl acrylate copolymers, acrylates/ammonium methacrylates copolymers, acrylates/$C_{12-22}$alkylmethacrylate copolymer, styrene/acrylates copolymers, acrylamide/acryloyldimethyltaurate copolymer, potassium acrylates/$C_{10-30}$alkyl acrylate crosspolymers, sodium acrylates/$C_{10-30}$alkyl acrylates crosspolymers, aminomethylpropanol-acrylate copolymer, glyceryl acrylate/acrylic acid copolymers, hydroxyethylacrylate/sodium acryloyldimethyl taurate copolymers, sodium hydroxyethylacrylate/acryloyldimethyltaurate copolymers, styrene/acrylates/ammonium methacrylate copolymers, sodium polyacrylates, sodium polyacrylate starches, polyglyceryl methacrylates, ammonium acryloyldimethyltaurate/VP copolymer or combinations thereof. In some embodiments, the acrylate component comprises an acrylates/ethylhexyl acrylate copolymer.

According to some embodiments, the charcoal component comprises a carbonaceous material derived from wood, bamboo, hardwood, peat, coal, coke, petroleum, bones, coconut shells, nutshells, coir, lignite or combinations thereof. The charcoal component may comprise activated charcoal, acid washed activated charcoal, high purity activated charcoal, impregnated charcoal, pharmaceutical grade activated charcoal, acid-washed granular activated charcoal made from coconut shell or combinations thereof. According to some embodiments, the charcoal component is in an amount of about 0.001 wt % to about 5 wt % based on a total weight of the adhesive composition. The charcoal component may comprise a plurality of units comprising powder, particles, granules, extrudates, pellets or combinations thereof. In some embodiments, the charcoal component comprises a plurality of units comprising a size of less than about 1 mm or comprising a mean size of about 1 mm. The charcoal component may comprise an activated charcoal powder.

The adhesive composition may comprise water. The water may be in an amount of about 1 wt % to about 90 wt % based on a total weight of the adhesive composition. The adhesive composition may comprise a colorant. The colorant may comprise carbon black, azo dye, quinophthalone dye, triphenylmethane dye, xanthene dye, iron oxide, iron hydroxide, titanium dioxide, sunset yellow dye, allura red dye, amaranth dye, koki neil red dye, azogeranin dye, tartrazine dye, brilliant black dye, canthaxanthin dye, patent blue dye, fast green dye, brilliant blue dye, acid green dye, erythrosine dye, quinoline yellow, indigotin, curcumin or combinations thereof.

In some embodiments, the adhesive composition may comprise a preservative. The preservative may comprise phenoxyethanol, benzalkonium chloride, sodium dehydroacetate, benzyl alcohol, phenethyl alcohol, phenoxyethanol, esters of p-hydroxybenzoic acid, imidazolidinyl urea, diazolidinyl urea, carboxylic acids or combinations thereof.

According to some embodiments, the adhesive composition is free of one or more of a cyanoacrylate, latex, a formaldehyde or any combination thereof. In some embodiments, the adhesive composition further comprises water, a colorant and a preservative. The adhesive composition may comprise the acrylate component in an amount of about 45 wt % to about 55 wt %, the charcoal component in an amount of about 0.001 wt % to about 2 wt %, the water in an amount of about 40 wt % to about 50 wt %, the colorant in an amount of about 1 wt % to about 4 wt % and the preservative in an amount of about 0.01 wt % to about 1.0 wt %. In some embodiments, the adhesive composition may include the acrylate component in an amount of about 51.5 wt %, the charcoal powder in an amount of about 0.5 wt %, the water in an amount of about 44.5 wt %, the colorant in an amount of about 3 wt % and the preservative in an amount of about 0.5 wt %. According to some embodiments, the acrylate component may be in an amount of about 51.5 wt %, the charcoal powder in an amount of less than about 0.99 wt %, the water in an amount of about 44.5 wt %, the colorant in an amount of about 3 wt % and the preservative in an amount of about 0.1 wt %. In some embodiments, the acrylate component comprises an acrylates/ethylhexyl acrylate copolymer, the charcoal component comprises an activated charcoal powder, and the adhesive composition further comprises water, phenoxyethanol, biotin and carbon black.

Embodiments of a method of manufacturing an adhesive composition for adhering lashes or lash extensions to an eye area as described herein may include mixing an acrylate component and a charcoal component, thereby forming the adhesive composition. In some embodiments, provided is a method of preparing an adhesive composition for application of one or more beauty article, comprises: combining a base with an acrylate component to form an acrylate mixture; and combining the acrylate mixture with a charcoal component to form the adhesive composition. The base may be combined with the acrylate component at a temperature of about 20° C. to about 40° C. In some embodiments, the base is formed by combining water, a preservative and a colorant. The water, preservative and colorant may be combined at a temperature of about 20° C. to about 40° C. According to some embodiments, the water, the preservative and the colorant are blended in a mixing tank for about 1 min to about 5 min to form a homogenous mixture. In some embodiments, the method of preparation may include adding the acrylate component to the mixing tank and mixing the acrylate component with the base (i.e., homogenous mixture) for about 1 min to about 30 min.

According to some embodiments, the adhesive composition prepared by the foregoing method of preparation comprises a viscosity of about 10,000 cP to about 50,000 cP as measured by American Society for Testing and Materials (ASTM) D 1084-97 at 25° C. The adhesive composition may comprise an adhesive strength to a surface of about 0.5 MPa to about 100 MPa.

In some embodiments, the acrylate component used in the method of preparation includes acrylates, polyacrylates, acrylamide polymers, alkyl acrylates, (meth)acrylates, acrylic acids, (meth)acrylic acid, acrylamide, (meth)acrylamide polymers, polymethacrylate, polymethylmethacrylate, $C_{1-6}$hydroxyalkyl (meth)acrylates, $C_{1-6}$alkoxy $C_{1-6}$alkyl (meth)acrylates, polyoxyalkylene (meth)acrylates, $C_{1-6}$alkylpolyoxyalkylene (meth)acrylates, $C_{8-22}$alkyl (meth)acrylates, methyl(meth)acrylate, ethyl(meth)acrylate, propyl(meth)acrylate, butyl(meth)acrylate, isobutyl(meth)acrylate, pentyl(meth)acrylate, hexyl(meth)acrylate, 2-hydroxyethyl(meth)acrylate, 2-methoxyethyl(meth)acrylate, polyoxyallcylene (meth)acrylates, polyethyleneglycol (meth)acrylate, polyethyleneglycol methyl ether (meth)acrylate, polyethyleneglycol ethyl ether (meth)acrylate, octyl(meth)acrylate, 2-ethylhexyl(meth)acrylate, lauryl (meth)acrylate, stearyl(meth)acrylate, 2-ethylhexyl acrylate, copolymers thereof, quaternary salts thereof, ethylhexyl acrylate copolymers, acrylates/ammonium methacrylates copolymers, acrylates/$C_{12-22}$alkylmethacrylate copolymer, styrene/acrylates copolymers, acrylamide/acryloyldimethyltaurate copolymer, potassium acrylates/$C_{10-30}$alkyl acrylate crosspolymers, sodium acrylates/$C_{10-30}$alkyl acrylates crosspolymers, aminomethylpropanol-acrylate copolymer, glyceryl acrylate/acrylic acid copolymers, hydroxyethylacrylate/sodium acryloyldimethyl tau rate copolymers, sodium hydroxyethylacrylate/acryloyldimethyl taurate copolymers, styrene/acrylates/ammonium methacrylate copolymers, sodium polyacrylates, sodium polyacrylate starches, polyglyceryl methacrylates, ammonium acryloyldimethyltaurate/VP copolymer or combinations thereof, and the charcoal component comprises activated charcoal, acid washed activated charcoal, high purity activated charcoal, impregnated charcoal, pharmaceutical grade activated charcoal, acid-washed granular activated charcoal made from coconut shell or combinations thereof.

Further described herein are kits, comprising: an adhesive composition for application of one or more beauty article, wherein the adhesive composition comprises an acrylate component and a charcoal component; a container configured to store the adhesive composition; and an applicator configured to apply the adhesive composition stored in the container to the one or more beauty article. According to some embodiments, the adhesive composition comprised within the kit is a pressure sensitive adhesive composition. According to some embodiments, the storage container comprises an opening that is configured to receive the applicator, the storage container is further configured to store at least a part of the applicator within the storage container in contact with the adhesive composition. The applicator may be coupled to a threaded cap configured to mate with a threaded collar of the storage container. In some embodiments, the applicator comprises a dispensing unit configured to apply the adhesive composition to at least one surface selected from a group consisting of natural lashes, natural beard, hair, skin, plastic, metal and combinations thereof. The dispensing unit may comprise a brush configured to apply the adhesive composition to the at least one surface. According to some embodiments, the container is comprised of a natural polymer, synthetic polymer, polyethylene, polypropylene, styrene, copolymers thereof or combinations thereof.

In some embodiments, the kit comprises at least one beauty article for application to a surface using the adhesive composition. The one or more beauty article may comprise one or more of a natural lash, a natural lash extension, an artificial lash, an artificial lash extension, a rhinestone, a gem, natural hair, artificial hair, paper, plastic, metal, glass, glitter and combinations thereof. In some embodiments, the one or more beauty article may comprise a lash or lash extension.

According to some embodiments, provided is a method of applying one or more of a lash or lash extension, comprising: applying an adhesive composition to an underside of natural lashes, wherein the adhesive composition comprises an acrylate component and a charcoal component; and applying the one or more lash or lash extension to the adhesive composition. The one or more lash or lash extension may comprise a natural lash, an artificial lash or a combination thereof. The method may comprise cleaning the natural lashes before applying the adhesive composition. Cleaning the natural lashes may comprise contacting the natural lashes with a cleaning solution. Contacting the natural lashes with the cleaning solution may comprise wetting a cotton pad with the cleaning solution and wiping the natural lashes or wetting a cleaning applicator with the cleaning solution and brushing the natural lashes or a combination thereof. In some embodiments, the cleaning applicator is a brush, spoolie, pick or combination thereof. The cleaning solution may comprise water, butylene glycol, pentylene glycol, polyethylene glycol, polyethylene glycol-6 caprylic/capric glycerides, polyethylene glycol-7 caprylic/capric glycerides, phenoxyethanol, lauryl betaine, sodium citrate, citric acid, or any combination thereof.

In some embodiments, the method of applying the one or more lash or lash extension further comprises retrieving the one or more lash or lash extension before applying the lash or lash extension to the adhesive composition. The one or more lash or lash extension may be retrieved from a container, a cartridge to which the one or more lash or lash extension is removably attached or a combination thereof. In some embodiments, retrieving the one or more lash or lash extension comprises removing the one or more lash or lash extension from the container using a lash applicator. The lash applicator may be a wand, pick, tweezers or a combination thereof applying the adhesive composition comprises distributing the adhesive composition on the underside of the natural lashes using an adhesive applicator. The adhesive applicator may comprise a spoolie, a brush, a pick or a combination thereof.

According to some embodiments, the method of applying the one or more lash or lash extension may further comprise drying the adhesive composition for about 10 seconds to about 2 minutes before applying the one or more lash or lash extension to the adhesive composition. Applying the one or more lash or lash extension to the adhesive composition may comprise applying pressure to the one or more lash or lash extension on the adhesive composition. Pressure may be applied for about 10 seconds to about 2 minutes. In some embodiments, the method may further comprise using a lash applicator to apply pressure to the one or more lash or lash extension on the adhesive composition. In some embodiments, covers (or sleeves) over the tips of the lash applicator may be used. The lash applicator may be a wand, pick, tweezers or a combination thereof. In some embodiments, applying the one or more lash or lash extension comprises arranging the one or more lash or lash extension on the adhesive composition. The arranging may comprise positioning the one or more lash or lash extension on the underside of the natural lashes.

According to some embodiments, the method of applying the one or more lash or lash extension may further comprise applying another layer of adhesive composition to the one or more lash or lash extension after applying the one or more lash or lash extension. The one or more lash or lash extension may remain applied to the adhesive composition for at least about 5 days.

DETAILED DESCRIPTION

Adhesive Compositions

Conventional lash adhesive compositions contain a variety of chemicals, including acrylates, formaldehyde, and latex. Given the sensitivity of the human eye, and the fumes emitted from these chemical components as the adhesive cures, many users experience irritation in and around the eye when applying lash adhesives. Additionally, many users experience an allergy or allergy-like reaction to lash adhesives.

In order to reduce or prevent these adverse reactions, users are advised to apply the adhesive in a well-ventilated room, and to take care in ensuring that the adhesive does not enter the eye. However, even when taking these precautions, many users still experience adverse reactions, such as allergic reactions to the chemicals in the adhesives. Other approaches to reducing or preventing the adverse reactions is to reduce the amount of chemicals in the adhesives, particularly through removal of latex and formaldehyde from certain adhesive compositions.

Aspects of the disclosure address the above and other challenges by providing adhesive compositions containing a charcoal component for adhering lashes or lash extensions. Adhesive compositions according to embodiments herein may have antibacterial and antimicrobial properties. The adhesive compositions may be waterproof and configured to absorb moisture and heat. According to some embodiments, adhesive compositions as described herein include an acrylate component and a charcoal component. The acrylate component can include any suitable acrylate, or combination of acrylates, that may be useful in artificial lash adhesives. Suitable materials for the acrylate component include, but are not limited to, acrylates, polyacrylates, acrylamide polymers, alkyl acrylates, (meth)acrylates, acrylic acids, (meth)acrylic acid, acryl amide, (meth)acrylamide polymers, polymethacrylate, polymethylmethacrylate, $C_{1-6}$hydroxyalkyl (meth)acrylates, $C_{1-6}$alkoxy $C_{1-6}$alkyl (meth)acrylates, polyoxyalkylene (meth)acrylates, $C_{1-6}$alkylpolyoxyalkylene (meth)acrylates, $C_{8-22}$alkyl (meth)acrylates, methyl(meth)acrylate, ethyl(meth)acrylate, propyl(meth)acrylate, butyl (meth)acrylate, isobutyl(meth)acrylate, pentyl(meth)acrylate, hexyl(meth)acrylate, 2-hydroxyethyl(meth)acrylate, 2-methoxyethyl(meth)acrylate, polyoxyallcylene (meth)acrylates, polyethyl eneglycol (meth)acrylate, polyethyleneglycol methyl ether (meth)acrylate, polyethyleneglycolethyl ether (meth)acrylate, octyl(meth)acrylate, 2-ethylhexyl(meth)acrylate, lauryl(meth)acrylate, stearyl (meth)acrylate, 2-ethylhexyl acrylate, copolymers thereof, quaternary salts thereof, ethylhexyl acrylate copolymers, acrylates/ammonium methacrylates copolymers, acrylates/$C_{12-22}$alkylmethacrylate copolymer, styrene/acrylates copolymers, acrylamide/acryloyldimethyltaurate copolymer, potassium acrylates/$C_{10-30}$alkyl acrylate crosspolymers, sodium acrylates/$C_{10-30}$alkyl acrylates crosspolymers, aminomethylpropanol-acrylate copolymer, glyceryl acrylate/acrylic acid copolymers, hydroxyethylacrylate/sodium acryloyldimethyl tau rate copolymers, sodium hydroxyethylacrylate/acryloyldimethyl taurate copolymers, styrene/acrylates/ammonium methacrylate copolymers, sodium polyacrylates, sodium polyacrylate starches, polyglyceryl methacrylates, ammonium acryloyldimethyltaurate/VP copolymer and/or combinations thereof. In some embodiments, the adhesive composition may include the acrylate component in an amount of about 10 percent by weight (wt %) to about 90 wt %, about 15 wt % to about 85 wt %, about 20 wt % to about 80 wt %, about 25 wt % to about 75 wt %, about 30 wt % to about 50 wt %, or about 45 wt % to about 55 wt % based on the total weight of the adhesive composition.

Without being bound by any particular theory, it is believed that when the acrylate component is mixed with activated charcoal, the resulting mixture may be more resistant to heat due to potentially absorbing the heat, and may adhere longer when exposed to heat, such as in a shower or other hot environment, as compared to conventional lash adhesives. The charcoal component can include any suitable charcoal material, or combination of charcoal materials. Charcoal, such as activated charcoal, refers to carbon that may be produced from carbonaceous materials such as wood (e.g., bamboo, hardwood, etc.), peat, coal, coke, petroleum, bones, coconut shells, nutshells, coir and lignite through, for example, physical reactivation (pyrolysis), chemical reactivation (combustion-treatment with strong acid, base or salt at high temperatures) and/or superheating of the carbonaceous materials. Suitable materials for the charcoal component of the adhesive compositions as described herein include, but are not limited to, activated charcoal, granular activated charcoal, extruded activated charcoal, pelletized activated charcoal, powdered activated charcoal, acid washed activated charcoal, high purity activated charcoal, impregnated charcoal, pharmaceutical grade activated charcoal, acid-washed granular activated charcoal made from coconut shell and/or combinations thereof. In some embodiments, the charcoal component is present in an amount of about 0.001 wt % to about 50 wt %, about 0.001 wt % to about 5 wt %, about 0.005 wt % to about 4 wt %, about 0.01 wt % to about 3 wt %, about 0.05 wt % to about 2 wt %, about 0.1 wt % to about 1 wt %, or about 2 wt %, about 5 wt %, about 10 wt %, about 15 wt %, about 20 wt % or about 30 wt % based on the total weight of the adhesive composition.

In some embodiments, the charcoal component is in the form of a plurality of units. The plurality of units may include, but are not limited to, powder, particles, granules, extrudates, pellets and/or combinations thereof. The plurality of units may have a size of less than about 1 millimeter (mm), less than about 0.75 mm, less than about 0.5 mm, less than about 0.25 mm, less than about 0.2 mm, less than about 0.1 mm, less than about 0.05 mm, or less than about 0.01 mm. In some embodiments, the plurality of units may have a mean size of about 1 mm, about 0.75 mm, about 0.5 mm, about 0.25 mm, about 0.2 mm, about 0.1 mm, about 0.05 mm, or about 0.01 mm.

Cyanoacrylates (e.g., octyl cyanoacrylate or known generically as instant glues, power glues or superglues) have been used in skin adhesives to address toxicity concerns and to reduce skin irritation and allergic responses. Despite these aims, when used as eyelash adhesives, cyanoacrylates can cause irritation to the eyes and surrounding skin and may trigger an allergic response. Latex-based glues are also used as skin adhesives, but some users are sensitive and/or allergic to latex. Formaldehydes, similarly, may be used in adhesives, but they are a skin and respiratory sensitizer and long-term exposure to formaldehydes can cause skin hardening, swelling, flaking, dermatitis, eczema, impaired lung function and cancer. Adhesive compositions according to some embodiments described herein may be free of one or more of cyanoacrylates, latex and/or formaldehydes.

Without being bound by any particular theory, it is believed that the charcoal component has antibacterial properties that may assist in reducing the potential for allergic reactions, such as inflammation, irritation, itchiness, soreness, redness, and/or infection in and around the eye. Additionally, the adhesive compositions with charcoal surprisingly exhibit less stickiness once the adhesive compositions are applied and dried, and thus may be preferred by users. A wide range of percentages of charcoal may be used in the formula, such as between 0.001% and 50%. The different ranges may alter the stickiness of the adhesive composition, and may further provide for different levels of antimicrobial action.

Adhesive compositions according to some embodiments may include a colorant. Suitable colorants include, but are not limited to, carbon black, azo dye, quinophthalone dye, triphenylmethane dye, xanthene dye, iron oxide, iron hydroxide, titanium dioxide, sunset yellow dye, allura red dye, amaranth dye, koki neil red dye, azogeranin dye, tartrazine dye, brilliant black dye, canthaxanthin dye, patent blue dye, fast green dye, brilliant blue dye, acid green dye, erythrosine dye, quinoline yellow, indigotin, curcumin and/or combinations thereof.

In further embodiments, the adhesive compositions include one or more preservatives, for example, having antibacterial properties. Such preservatives may include, but are not limited to, phenoxyethanol, benzalkonium chloride, sodium dehydroacetate, benzyl alcohol, phenethyl alcohol, phenoxyethanol, esters of p-hydroxybenzoic acid, imidazolidinyl urea, diazolidinyl urea, carboxylic acids and/or combinations thereof. Other types of preservatives or weak preservatives, such as ethylhexylgycerin, caprylyl glycol, any other preservative, or any combination thereof in safe and approved by regulatory bodies may be utilized in safe levels. Adhesive compositions according to some embodiments may include one or more preservatives in an amount of about 0.1 wt % to about 10 wt %. In some embodiments, the amount of the one or more preservative may be about 1 wt % or less, about 3 wt % or less, or otherwise. In some embodiments, the preservative is phenoxyethanol. In such compositions, the amount of phenoxyethanol may less than about 0.1 wt %, where being about 0.1 wt % means that the amount of phenoxyethanol may be slightly higher than 0.1 wt %, such as 10 wt % (i.e., 0.11 wt %). Depending on the composition, the amount of the one or more preservative may be about 1 wt % or less, about 3 wt % or less, or otherwise.

In some embodiments, the adhesive composition may include water in an amount of about 1 wt % to about 90 wt %, about 5 wt % to about 80 wt % or about 40 wt % to about 50 wt % based on the total weight of the adhesive composition. Adhesive compositions as described herein may include water-soluble vitamins including, but not limited to, vitamin thiamin (e.g., vitamin B1), riboflavin (e.g., vitamin B2), niacin (e.g., vitamin B3), vitamin B6, folate (e.g., vitamin B9), vitamin B12 (e.g., a methylcobalamin), biotin (e.g., vitamin B7), pantothenic acid (e.g., vitamin B5), derivatives thereof and/or combinations thereof. In some embodiments, the adhesive compositions may include water soluble vitamins in an amount of about 0.1 wt % to about 20 wt %, about 0.5 wt % to about 15 wt % or about 1 wt % to about 15 wt % based on the total weight of the adhesive composition. According to some embodiments, the adhesive compositions may contain latex. The latex may be present in an amount of about 0 wt % to about 80 wt %, or about 0.1 wt % to about 75 wt %, or about 0.5 wt % to about 60 wt %, or about 1 wt % to about 50 wt % based on the total weight of the adhesive composition.

In an illustrative embodiment, the adhesive composition may include the acrylate component in an amount of about 45 wt % to about 55 wt %, the water in an amount of about 40 wt % to about 50 wt %, the colorant in an amount of about 1 wt % to about 4 wt %, the preservative in an amount of about 0.10 wt % to about 1.0 wt % and the charcoal component (e.g., activated charcoal powder) in an amount of about 0.10 wt % to about 1 wt %. In some embodiments, the acrylate component is in an amount of about 45 wt % to about 55 wt %, the charcoal component is in an amount of about 0.001 wt % to about 2 wt %, the water is in an amount of about 40 wt % to about 50 wt %, the colorant is in an amount of about 1 wt % to about 4 wt % and the preservative is in an amount of about 0.01 wt % to about 1.0 wt %. In an illustrative embodiment, the adhesive compositions may include an acrylates/ethylhexyl acrylate copolymer, water, charcoal powder (e.g., activated charcoal powder), phenoxyethanol, biotin and carbon black. In embodiments, the adhesive composition is a pressure sensitive adhesive that enables a user to press the adhesive composition onto surfaces to adhere beauty articles thereto.

Adhesive compositions according to embodiments herein may have an adhesive strength suitable for attaching eyelashes or other embellishment to skin or other surfaces. Adhesive strength may refer to the ability of an adhesive to stick to a surface and bond two surfaces together. It may be measured by determining the maximum tensile stress needed to detach or unstick the adhesive perpendicular to the substrate. The adhesive strength may be the maximum tensile stress possible at the interface. According to some embodiments, the adhesive strength of the adhesive composition to skin or other surfaces is about 0.5 MPa to about 100 MPa, about 1 MPa to about 50 MPa, about 1 MPa to about 25 MPa. In some embodiments, the adhesive compositions according to embodiments herein may have a peel strength of about 1 kN/m to about 25 kN/m, or about 3 kN/m to about 10 kN/m. According to some embodiments, the adhesive composition prior to drying may have a viscosity of about 10,000 cP to about 50,000 cP as measured by ASTM D 1084-97 Standard Test Method for Viscosity of Adhesives.

Kits

Further disclosed are kits including the adhesive composition as described herein and an applicator. With reference to FIG. 1, a kit 100 according to some embodiments may include a container 102 for housing and/or storing the adhesive composition. Container 102 may include a collar 106 such as a threaded collar, that defines an opening 104 configured to receive applicator 108. Collar 106 may be configured to mate with a corresponding cap 110, such as a threaded cap, of applicator 108. Applicator 108 may include a dispensing unit 112 configured to evenly spread the adhesive composition, for example, onto the underside of the natural lashes. In some embodiments, any suitable type of dispensing unit 112 may be used to apply and spread the adhesive composition. Suitable dispensing units include, but are not limited to, a brush, a stick, a paddle, a swab, foam, a pick or combinations thereof. Container 102 may be formed of any suitable material. Suitable materials for container 102 include, but are not limited to, natural polymers, synthetic polymers, polyethylene, polypropylene, styrene, copolymers thereof and/or combinations thereof.

In some embodiments, kit 100 may further include at least one article such as a beauty article for application to a surface using the adhesive composition. Suitable beauty articles include, but are not limited to, a lash (e.g., an individual lash), a lash extension (e.g., a cluster of individual lashes), rhinestones, gems, hair, artificial hair, paper, plastic, metal, glass, glitter and/or combinations thereof. The lash or lash extension may be formed of natural human or animal hair or of artificial hair. In at least one embodiment, the at least one beauty article is a one or more of a lash or lash extension (natural or artificial). The adhesive composition may be a pressure sensitive adhesive composition so that after applying the adhesive composition to the at least one beauty article, the article may be pressed onto a surface, such as a user's eyelid, and permitted to dry and adhere to the surface.

Figure 2:
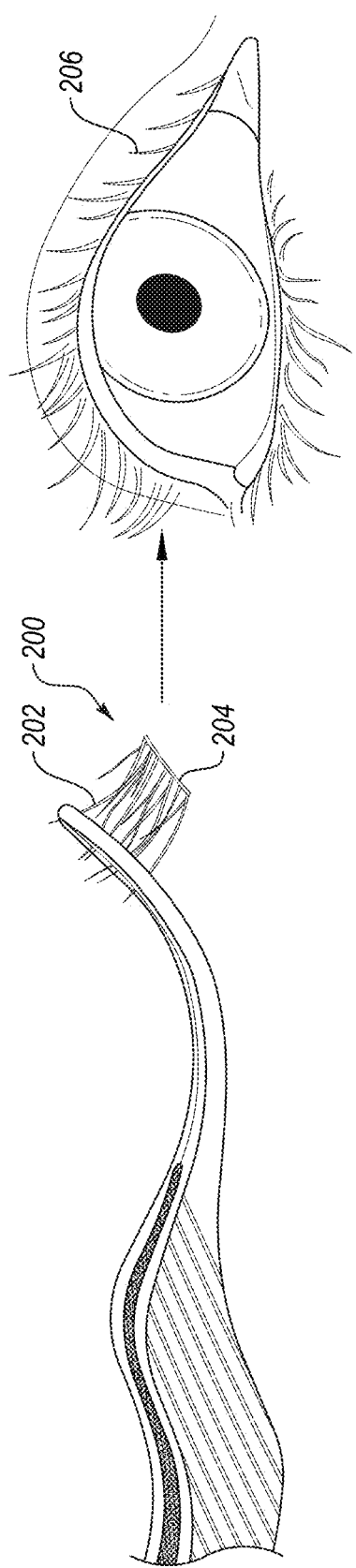
FIG. 2 illustrates an example embodiment of a kit containing lashes or lash extensions having an adhesive composition, according to some embodiments herein, attached thereto.

With reference to FIG. 2, according to some embodiments, a kit 200 includes one or more lash extensions 202 having an adhesive composition 204 pre-attached thereto (e.g., for press-on application). In some embodiments, the adhesive composition 204 may not be pre-attached to the lash extension 202, but may be stored in a container and applied using an applicator as shown and described with respect to FIG. 1. The one or more lash extensions 202 and adhesive composition 204 may be packaged together. In some embodiments, the one or more lash extensions 202 with the adhesive composition 204 attached thereto may be sealed in one or more airtight compartment to prevent drying of the adhesive composition 204. When a user opens a compartment, for example, by peeling away a plastic film cover, the adhesive composition 204 may be tacky and capable of adhering to surfaces such as skin. In some embodiments, kit 200 includes a lash applicator 208 for holding and applying the one or more lash extensions 202. Using the lash applicator 208, a user may arrange the one or more lash extensions 202 on an underside of the natural lashes 206 and press the one or more lash extensions 202 and the adhesive composition onto the natural lashes 206. The user may continue pressing on the eyelashes for about 1 min to about 5 min while allowing the adhesive composition to bond to the one or more lash extensions 202 and the natural lashes 206.

Figure 7:
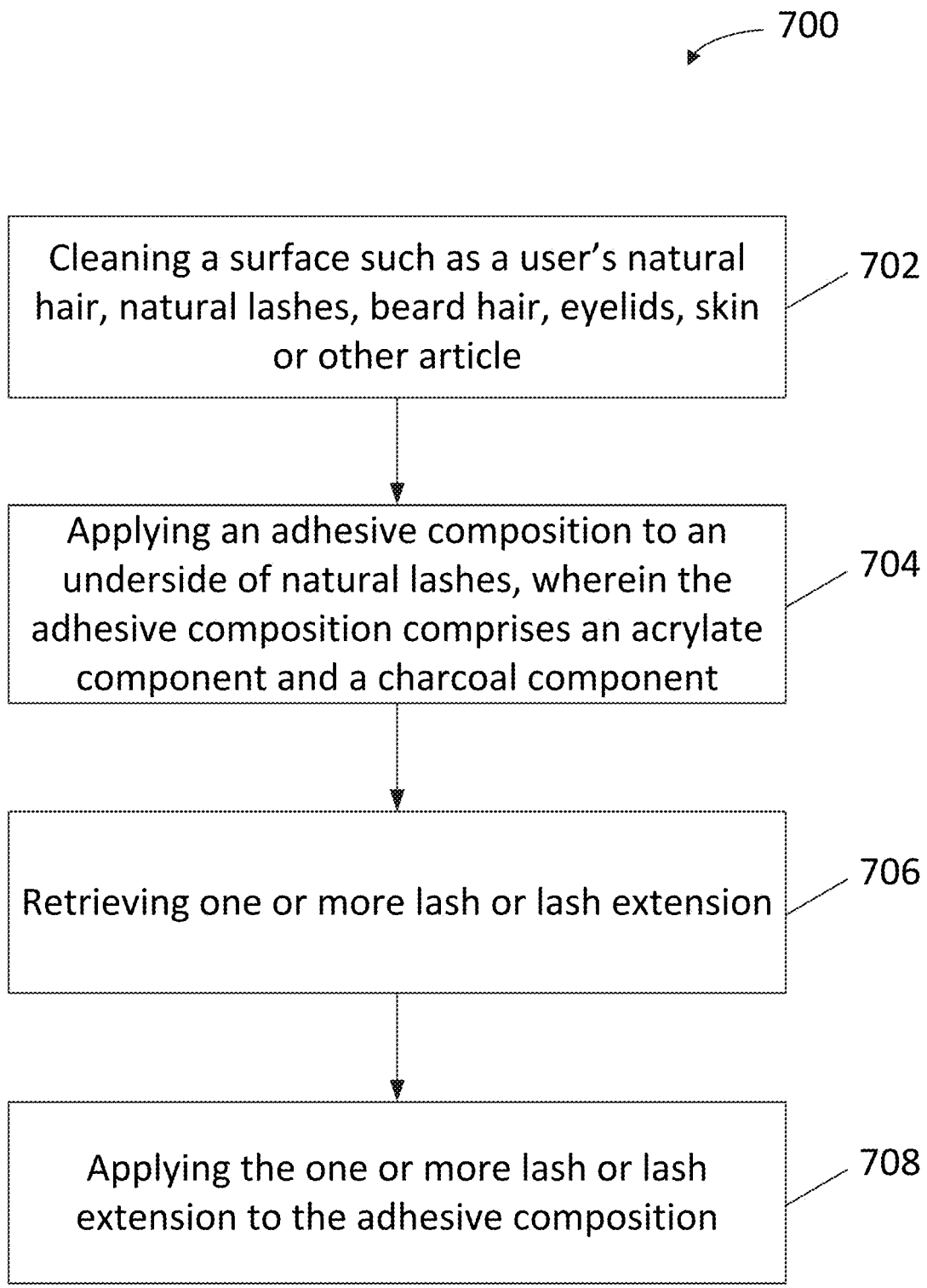
FIG. 7 illustrates an embodiment of a method of using an adhesive composition as described herein.

Kits according to various embodiments herein may include the adhesive composition and any other suitable embellishments and/or lashes or lash extensions as described herein. Kits according to various embodiments herein may include: one or more lash or lash extension, for example, wherein the one or more lash or lash extension is within in a container, a cartridge assembly described with respect to FIG. 8, or where the cartridge assembly having the one or more lash or lash extension removably attached thereto is within a container. Kits may further include an adhesive composition, for example, stored within a container as shown and described with respect to FIG. 1, and an applicator also as shown and described with respect to FIG. 1. In some embodiments, the kits may include a cleaning solution as described herein and optionally a cleaning applicator such as a pad, cloth or spoolie for applying the cleaning solution to the natural lashes. Kits as described herein may include any suitable lash applicator such as lash applicator 900 described with respect to FIG. 9. In some embodiments, the kits may include instructions describing one or more of the blocks of method 700 as shown in FIG. 7.

Methods of Preparation

Figure 3:
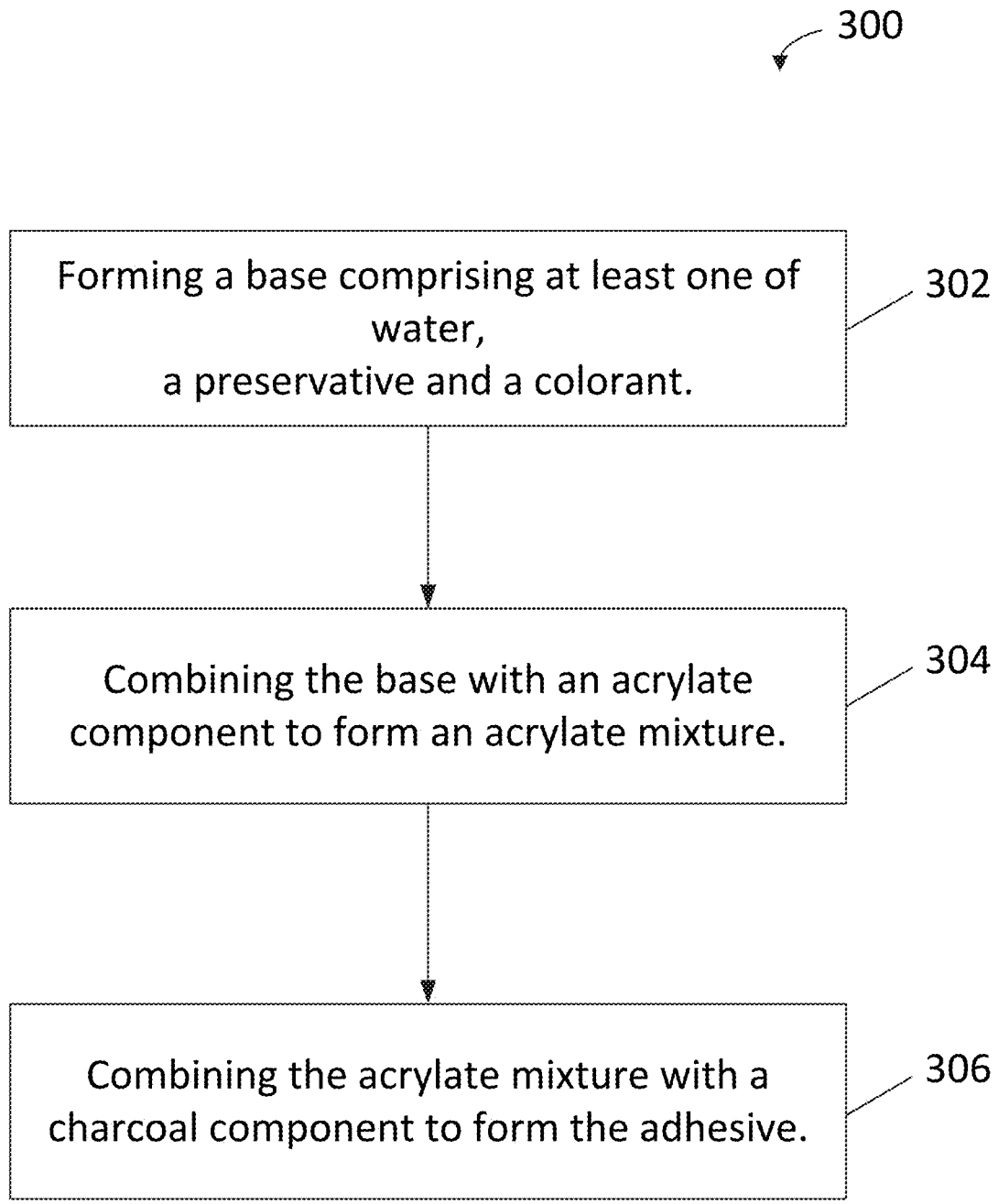
FIG. 3 illustrates an embodiment of a method of preparing an adhesive composition as described herein.

Further described are methods for preparing adhesive compositions according to various embodiments herein. With reference to FIG. 3, in some embodiments a method 300 may include at block 302 forming a base, for example, a liquid solution suitable for dissolving other components. In some embodiments, the base may be formed by combining one or more of water, a preservative as described herein and/or a colorant as described herein in a mixing vessel. Suitable mixing vessels include, but are not limited to, beakers, tanks, blenders, drums, reservoirs and/or any other suitable mixing vessel for combining liquid components or liquid and solid components. The base components may be mixed using any suitable mixing device and method including, but not limited to, dynamic mixing, static mixing, a paddle mixer, pump recirculation, sparging, jet mixing and any combination thereof. The base may be a homogenous mixture of the one or more component. According to some embodiments, the one or more component, for example, water, preservative and/or colorant, may be blended in the mixing vessel for about 1 min to about 5 min to form the homogenous mixture. In some embodiments, the base may be formed at a temperature of about 20° C. to about 40° C. and at atmospheric pressure.

At block 304, method 300 may include combining the base with an acrylate component as described herein to form an acrylate mixture. The acrylate component may be added to the base in the above-described mixing vessel and stirred using the above-described mixing device. The acrylate mixture may be a homogenous mixture of the base and the acrylate component. In some embodiments, the base may be combined with the acrylate component at a temperature of about 20° C. to about 40° C. and at atmospheric pressure. In some embodiments, method 300 may include adding the acrylate component to the mixing tank containing the base and mixing the acrylate component with the homogenous mixture for about 1 min to about 30 min.

At block 306, method 300 may include combining the acrylate mixture with a charcoal component as described herein to form the adhesive composition. The charcoal component may be combined with the acrylate mixture in the mixing vessel and using the mixing device as described above. Upon formation, the adhesive composition may be a flowable liquid, for example, having a viscosity of about 10,000 cP to about 50,000 cP as measured by ASTM D 1084-97 Standard Test Method for Viscosity of Adhesives when measured at, for example, a temperature of about 20° C. or about 25° C. and atmospheric pressure.

Methods of Use

Disclosed herein are methods of using adhesive compositions as described herein to adhere articles to surfaces. Adhesive compositions as described herein may be suitable for long wear and flexible hold of eyelashes and other articles to surfaces such as skin, plastic, metal and/or mannequins. The adhesive compositions disclosed herein may be used to adhere a variety of types of lashes (e.g., individual lashes) or lash extensions to an eye area, including natural and artificial lashes and lash extensions (e.g., clusters of artificial lashes, strips of artificial lashes) and so forth. In use, the adhesives disclosed herein may be applied to the underside of a user's natural lashes, lash line, skin and/or combinations thereof. In some embodiments, the adhesive compositions as disclosed herein may be used to adhere other embellishments to surfaces, including, but not limited to, rhinestones, gems, hair, artificial hair, paper articles, plastic articles, metal articles, glass articles, glitter and/or combinations thereof.

When applied onto natural lashes or other hair, the adhesive compositions may keep a user's lashes healthy and hygienic and may also color the natural lashes or other hair, for example, black. The adhesive compositions may withstand heat, bacteria and microbes and may absorb excess moisture. In embodiments, the adhesive compositions may include biotin to nourish the natural lashes. Adhesive compositions according to some embodiments herein may enable a user to wear lashes (or other embellishments) for one or more days, for example, at least about 2 days, at least about 3 days, at least about 4 days, at least about 5 days, at least about 6 days, at least about 7 days, at least about 8 days, at least about 9 days, at least about 10 days and so on. The adhesive compositions according to some embodiments may be waterproof. For example, a user can wear lashes or lash extensions that have been bonded to the user's natural lashes using the adhesive compositions as described herein while taking a shower or swimming while maintaining the bond.

Figure 4:
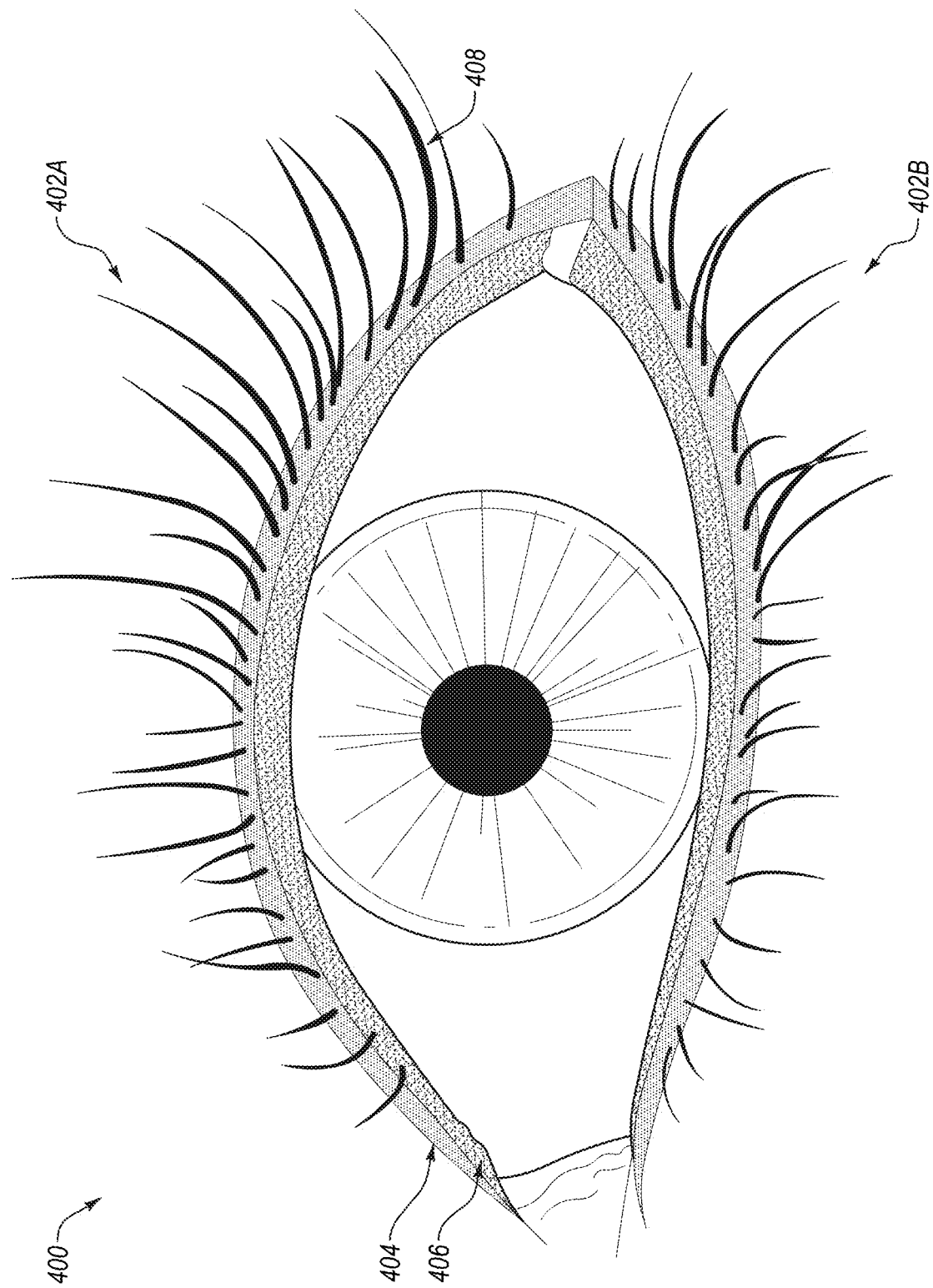
FIG. 4 is an illustration of an eye area, in accordance with some embodiments of the disclosure.

FIG. 4 is an illustration of an eye area, in accordance with some embodiments of the disclosure. As shown in FIG. 4, the eye area 400, such as a human eye area, can include upper natural lashes 402A (also referred to as "natural lashes 402A" or "natural lash 402A" herein) and lower natural lashes 402B (also referred to as "natural lashes 402B" or "natural lash 402B" herein). Natural lashes 402A and 402B can have an underside and topside. For example, natural lashes 402A show an underside 408. Natural lashes 402B show a topside. Natural lashes 402A and 402B are collectively referred to as natural lashes 402, herein.

The eye area 400 includes an upper lash line 404 (also referred to as "lash line 404" herein) and upper waterline 406 (also referred to as "waterline 406" herein). In some embodiments, a lash line, such as the upper lash line 404 or lower lash line of natural lashes 402B, can include the area between the natural lashes. The lash line can be curved and follow the alignment of the natural lashes 402. In some embodiments, the upper lash line 404 can include some area of the skin that is above (e.g., directly above) the natural lashes 402A. Similarly, the lower lash line can include some area of the skin that is below (e.g., directly below) the natural lashes 402B. In some embodiments, the waterline (also referred to as "wetline"), such as upper water line 406 and lower water line corresponding to natural lashes 402B, can include an area (or line) of skin that is exposed between the natural lashes 402 and the eye.

Spatially relative terms, such as "under," "upper" "lower," "top," "bottom," and so forth as used herein refer to a relative position of one element with respect to another element. Unless otherwise specified, the spatially relative terms are not intended to be limiting to the absolute orientation, and are intended to encompass different orientations (e.g., rotated 90 degrees, inverted, flipped) of elements in addition to the orientation depicted in the Figures. For example, if elements in the Figures are inverted, elements described as "upper" elements can then be considered oriented as "lower" elements, without deviating from aspects of the disclosure.

Figure 5:
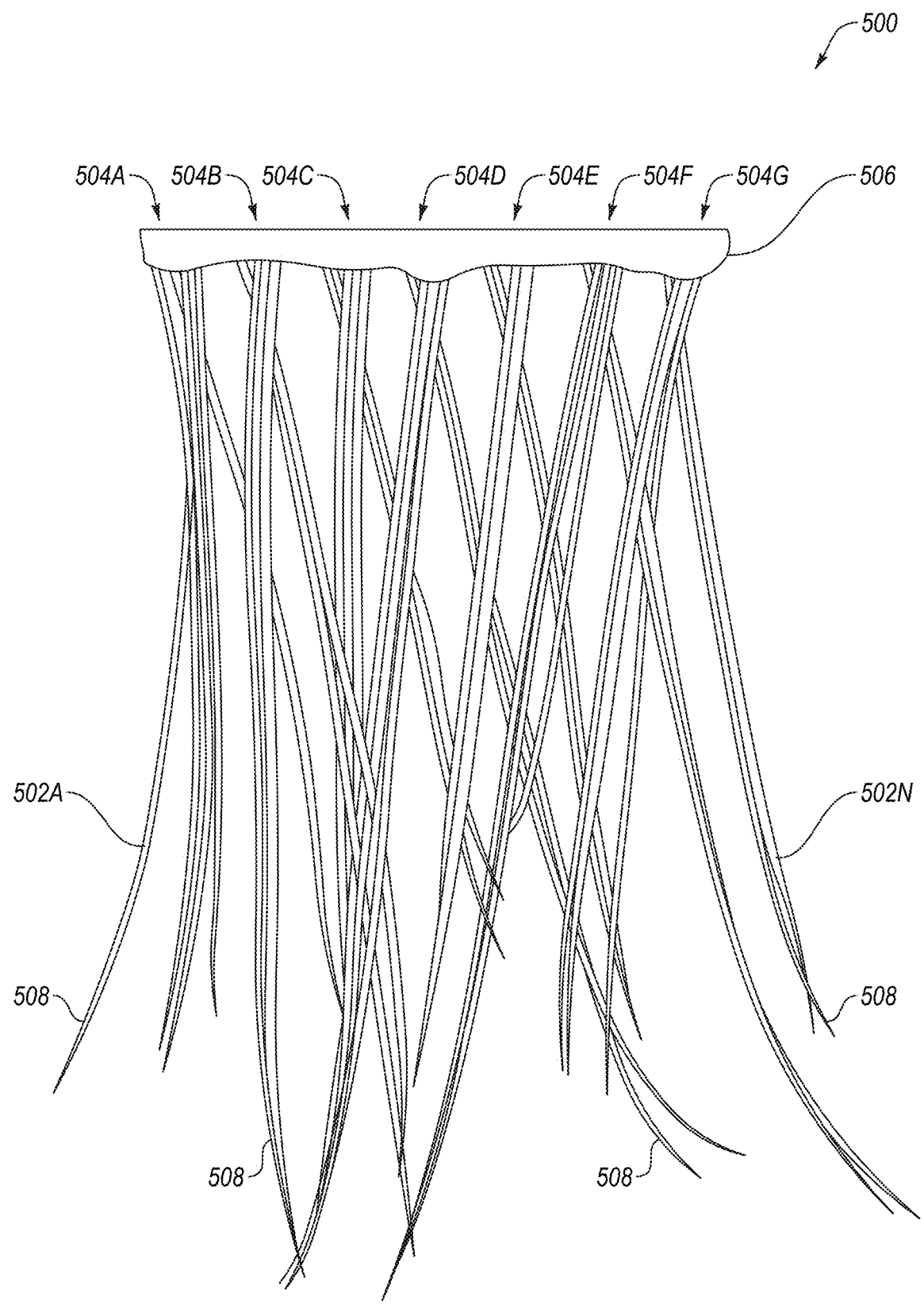
FIG. 5 is an illustration of an exemplary artificial lash extension, in accordance with some embodiments of the disclosure.
Figure 6:
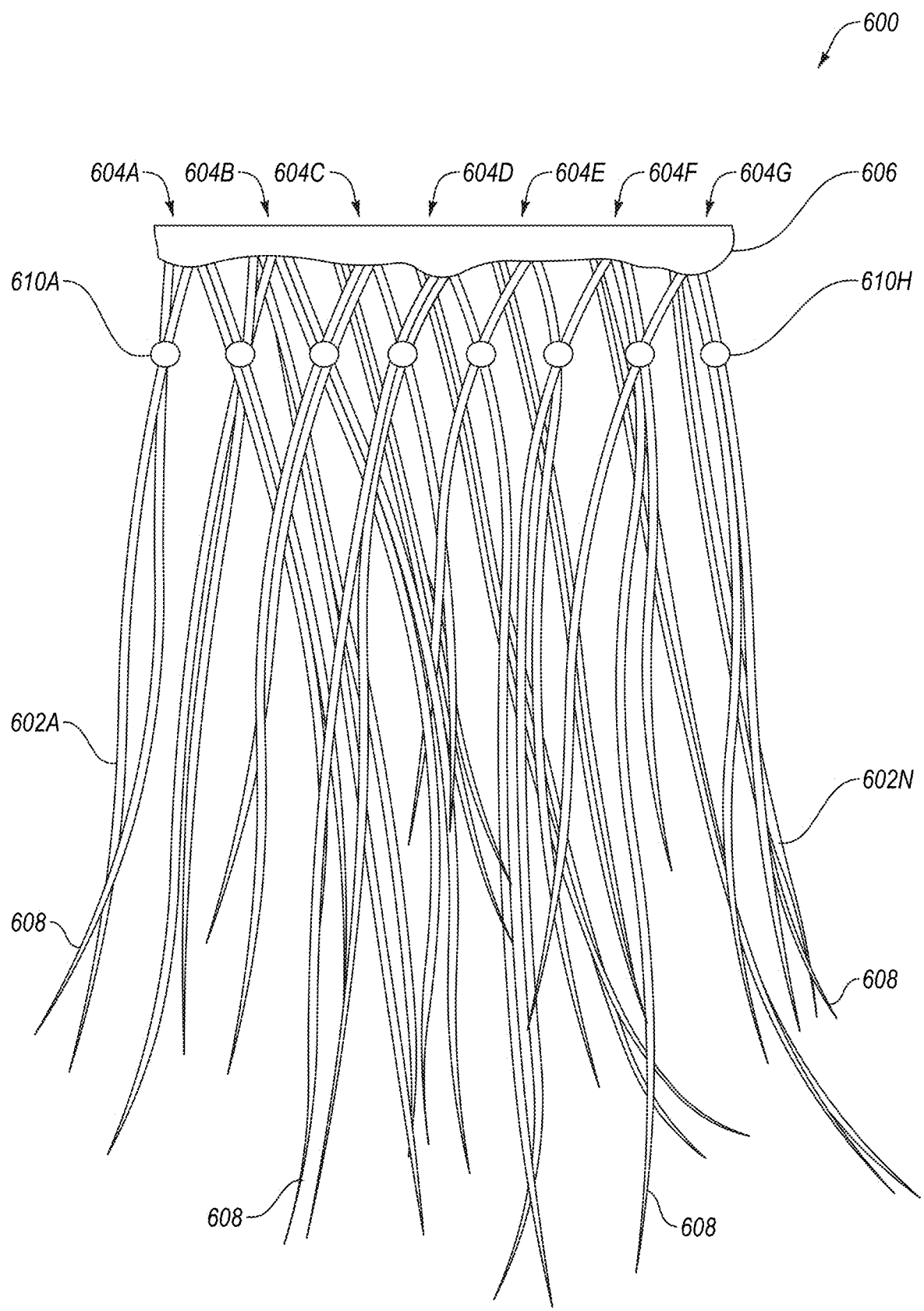
FIG. 6 is an illustration of another exemplary artificial lash extension, in accordance with some embodiments of the disclosure.

FIG. 5 is an illustration of an exemplary artificial lash extension, in accordance with some embodiments of the disclosure. FIG. 6 is an illustration of another exemplary artificial lash extension, in accordance with some embodiments of the disclosure.

In some embodiments, one or more of artificial lash extension 500 or artificial lash extension 600 (both also referred to as "lash extension" or "artificial eyelash extension" herein) are designed or configured for application at the underside of a natural lash. In some embodiments, one or more of artificial lash extension 500 or artificial lash extension 600 can be part of a set of multiple artificial lash extensions. In some embodiments, one or more of artificial lash extension 500 or artificial lash extension 600 can be a segment of a "full" artificial lash extension such that when multiple artificial lash extensions are arranged adjacent to one another at the underside of a natural lash (e.g., natural lashes 402A) the arranged artificial lash extensions span the length of the natural lash. The artificial lash extension can be arranged to substantially align with the lash line of the user. Using artificial lash extensions that are independent segments can allow an individual artificial lash extension to move independently when bonded to the underside of a natural lash, which mimics the movement of the natural lash and can improve the feel, comfort, and longevity of the artificial lash extensions.

Artificial lash extension 500 and artificial lash extension 600 respectively depict artificial hairs 502A-502N (collectively referred to as "artificial hairs 502" herein) and 602A-602N (collectively referred to as "artificial hairs 602" herein). In some embodiments, the artificial hairs of an artificial lash extension, such as artificial lash extension 500 or artificial lash extension 600, can be formed from one or more synthetic materials, including but not limited to polybutylene terephthalate (PBT), acrylic resin, polyester, or other synthetic material. In alternative embodiments, a natural material such as natural hair (e.g., human hair or mink hair) can be used. In some embodiments, the artificial hairs of a particular artificial lash extension can have one or more lengths and/or one or more diameters. In some embodiments, the diameter of an artificial hair can be between approximately 0.0075 millimeters (mm) (e.g., 0.0075 mm+/− 0.0025 mm) to 0.3 mm (e.g., 0.3 mm+/− 0.05 mm). In some embodiments, the ends of one or more of the artificial hairs can be tapered. In some embodiments, the one or more of artificial hairs can be curled or shaped in particular direction. For example, the ends 508 of artificial hairs 502 or the ends 608 of artificial hairs 602 can be tapered or curled or both. In some embodiments, the artificial hairs can range from 3 mm to 30 mm in length or in some instances even longer.

In some embodiments, one or more of artificial lash extension 500 or artificial lash extension 600 can include a base, such as base 506 and base 606, respectively. The base can include a top side (e.g., facing out of the page and towards the reader), a bottom side, a back side, a front side, and two lateral sides. In some embodiments, one or more of the multiple artificial hairs of artificial lash extension protrude out the front side of the base. When arranged at the underside of a natural lash, the backside of the artificial lash extension can point towards the user's eye. The thickness (e.g., between the topside and bottom side of the base can be between approximately 0.05 millimeters (mm) and approximately 0.15 mm (e.g., 0.05 mm+/− 0.01 mm). The low profile of the base is designed to allow the artificial lash extension to be light weight so as to better adhere to the underside of the natural lash and prevent obstruction of a user's view. The low profile of the base can at least in part be attributed to an application of heat in the formation of the base.

In some embodiments, one or more of the top side or bottom side (e.g., surface) of the base is substantially flat (e.g., having a flatness control tolerance value of +/− 0.03 mm or +/− 0.015 mm). In some embodiments, the flatness of the base of the artificial lash extension 500 is designed to allow improved contact and adhesion to a surface, such as the underside of a natural lash or the opposing surface of another artificial lash extension. The flatness of the base can at least in part be attributed to an application of heat in the formation of the base.

In some embodiments, the base can be formed by an application of heat at or near the area of the base to be formed. The application of heat can cause one or more of the artificial hairs (e.g. all of the artificial hairs) of an artificial lash extension to be connected to the base. In some embodiments, a heated fixture, such a heated platen, a heated crimp, heating lamp or other device can be used (e.g., pressed against the artificial hairs) to at least partially melt at least some of the artificial hairs. In some embodiments, the at least partially melted artificial hairs at least in part, or in full, form the base. In some embodiments, the at least partially melted artificial hairs melt in manner that connects the multiple artificial hairs to the base of the artificial lash extension.

In some embodiments, some additional artificial material, such as one or more artificial hairs or other material can be placed orthogonal to the artificial hairs at the area where the base is to be formed. Heat can be applied to the area of where the base is to be formed (which includes the additional artificial material). One or more of the artificial hairs or the additional artificial material can at least partially melt to at least in part, or in full, form the base. In some embodiments, the additional artificial material can include an adhesive (e.g. application of adhesive) and/or support thread. In some embodiments, the application of heat can be used to help cure the applied adhesive. In some embodiments that use an adhesive with the application of heat may or may not partially melt the artificial hairs.

In some embodiments, prior to the application of heat the artificial hairs may be tied (e.g., knotted) to a support or base thread or fiber to align the artificial hairs and prevent the horizontal spreading of the artificial hairs. Heat can be applied as described above (while the artificial hairs are knotted to a support thread) such that the support thread forms part of the base. In other instances, heat can be applied below the horizontal support thread. For instance, the support thread can hold the artificial hairs in place and the application heat can form a base below the support thread. In other embodiments, the artificial hairs are not aligned with a support thread (e.g., are not knotted on a support thread) before or during the formation of the base using the application of heat. In other embodiments, the artificial hairs can be arranged using a stencil or other arrangement device before or during the formation of the base using the application of heat. In some embodiments, one or more applications of heat can be performed to form the base. In an alternative embodiment, the base can be formed in part or in full using a chemical process.

In some embodiments, one or more of artificial lash extension 500 and artificial lash extension 600 include artificial hairs 502 and 602 that are respectively configured into clusters 504A-504G (collectively referred to as "clusters 504" herein) and 604A-604G (collectively referred to as "clusters 604" herein). In some embodiments, a cluster of hairs can refer to two or more artificial hairs that are grouped together. In some embodiments, 3-30 artificial hairs can be included in a cluster. In some embodiments, one or more individual clusters of artificial hairs can be formed using an application of heat as described above. Thus, the clusters can have a base (e.g., cluster base). The clusters can be arranged and heat can be applied, as described above, to the cluster bases to form another base (e.g., artificial lash extension base). In some embodiments, the artificial lash extension is formed without creating clusters using the application of heat. In some embodiments, at least two artificial hairs of an artificial lash extension crisscross each other. For example, two artificial hairs of a particular cluster can crisscross one another.

In some embodiments, artificial lash extensions 500 or 600 may be 4-10 mm wide, though embodiments may be 5-6 mm wide. In some embodiments, this is much wider than single clusters that are typically 1.5-2 mm wide, and thus provide greater coverage of the natural lash.

Artificial lash extension 600 further illustrates adjacent artificial hairs (or adjacent clusters 604) that are coupled or secured to one another at intersecting portions 610A-610K (collectively referred to as "intersecting portions 610" herein) of the crisscrossing artificial hairs 602. The intersecting portions 610 can be coupled or secured to one another using one or more of an application of heat, an application of adhesive, or a chemical process as described herein. In some embodiments, the intersecting portions 610 can be formed after or during the formation of the base. For example, the crisscrossing artificial hairs 602 are connected or secured together approximately 1 mm to approximately 5 mm (+/−0.5 mm) above the base 606. In some embodiments, the base 606 can be removed after the formation of the intersecting portions 610, such that the artificial lash extension 600 does not include the base 606. The secured intersecting portions 610 can hold artificial hairs 602 of the artificial lash extension 600 together in the absence of base 606. In some embodiments, base 606 in not formed. The intersecting portions 610 of the crisscrossing artificial hairs 602 can be formed without forming a base 606.

With reference to FIG. 7, disclosed herein is a method 700 of applying one or more of a lash or lash extension. The lash or lash extension may be formed of natural hair (e.g., natural lash hair) or artificial materials (e.g., an artificial lash extension as described herein). A lash may be a single lash, a plurality of which may be applied individually to an upper lash line to enhance the eye area.

In some embodiments, method 700 includes, at block 702, optionally, cleaning a surface such as a user's natural hair, natural lashes, beard hair, lash line, eyelid, skin or other article (e.g., a mannequin, a plastic, a metal and so on) before applying the adhesive composition. In some embodiments, the method includes cleaning a user's natural lashes before applying the adhesive composition to an underside of the natural lashes. Cleaning the natural lashes may include contacting the natural lashes with a cleaning solution. A suitable cleaning solution may include water, butylene glycol, pentylene glycol, polyethylene glycol, polyethylene glycol-6 caprylic/capric glycerides, polyethylene glycol-7 caprylic/capric glycerides, phenoxyethanol, lauryl betaine, sodium citrate, citric acid, or combinations thereof. In some embodiments, contacting the natural lashes with the cleaning solution includes wetting a pad (e.g., a disposable cotton pad) or cloth (e.g., a wash cloth) with the cleaning solution and wiping the natural lashes, lash line, eyelid, skin or combinations thereof with the cleaning solution. In some embodiments, contacting the natural lashes with the cleaning solution can include wetting a cleaning applicator with the cleaning solution and brushing the natural lashes with the cleaning solution. In some embodiments, contacting the surface with the cleaning solution may include both wiping with a pad or cloth and brushing with a cleaning applicator. Suitable cleaning applicators include, but are not limited to, a brush, spoolie (e.g., a disposable or reusable mascara brush), pick or combination thereof.

At block 704, method 700 may include, applying an adhesive composition as described herein to the surface. In some embodiments, the adhesive composition may be applied to an underside of the natural lashes, which may or may not have been cleaned as described with respect to block 702. The adhesive composition may include an acrylate component and a charcoal component according to various aspects of the adhesive composition described herein. In some embodiments, the adhesive composition may be applied to the one or more lash or lash extension instead of or in combination with the natural lashes.

According to some embodiments, applying the adhesive composition to the surface includes distributing the adhesive composition on the underside of the natural lashes using an adhesive applicator. The term "distributing" includes spreading, brushing, or otherwise covering, at least partially, the surface with the adhesive composition. Suitable adhesive applicators for distributing adhesive composition onto a surface include, but are not limited to, a spoolie, a brush, a pick or a combination thereof. Applying the adhesive composition onto the surface may include, in some embodiments, drying the adhesive composition for about 10 seconds to about 2 minutes before applying the one or more lash or lash extension to the adhesive composition.

Figure 8A:
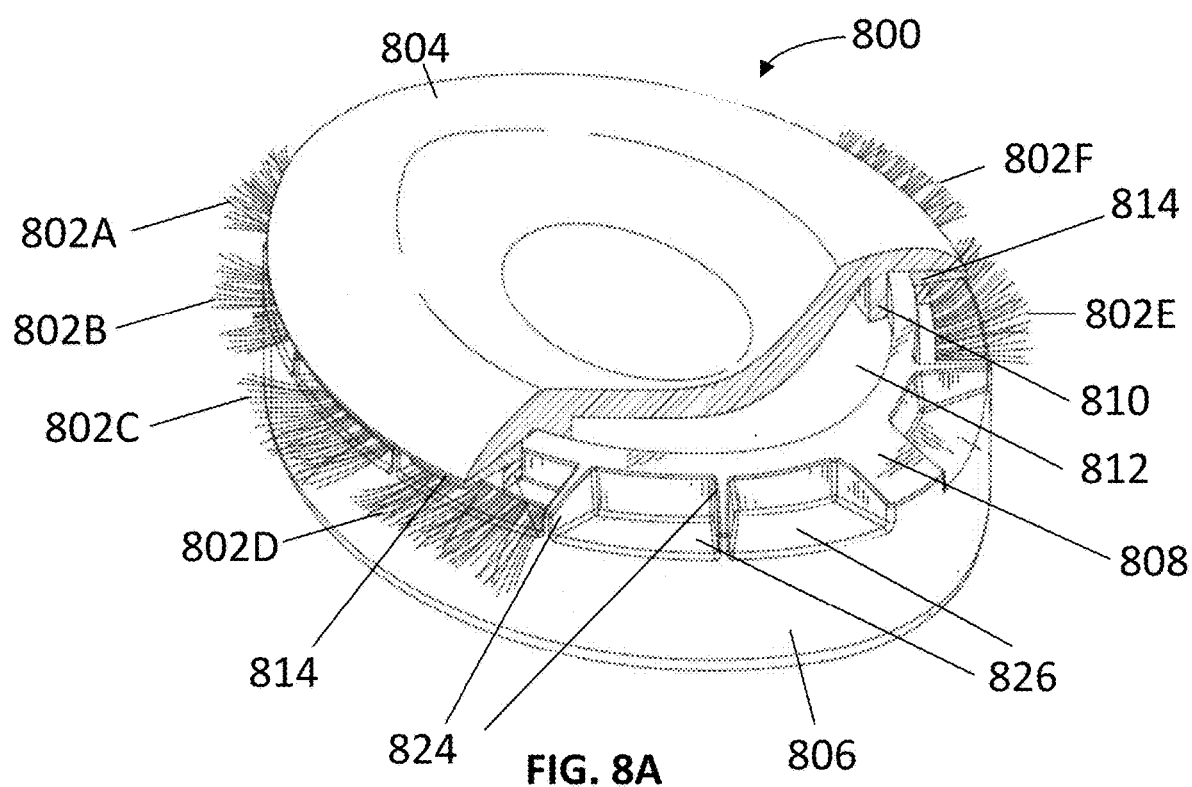
FIG. 8A illustrates an embodiment of a cartridge assembly for storing a lash or lash extension as described herein.
Figure 8B:
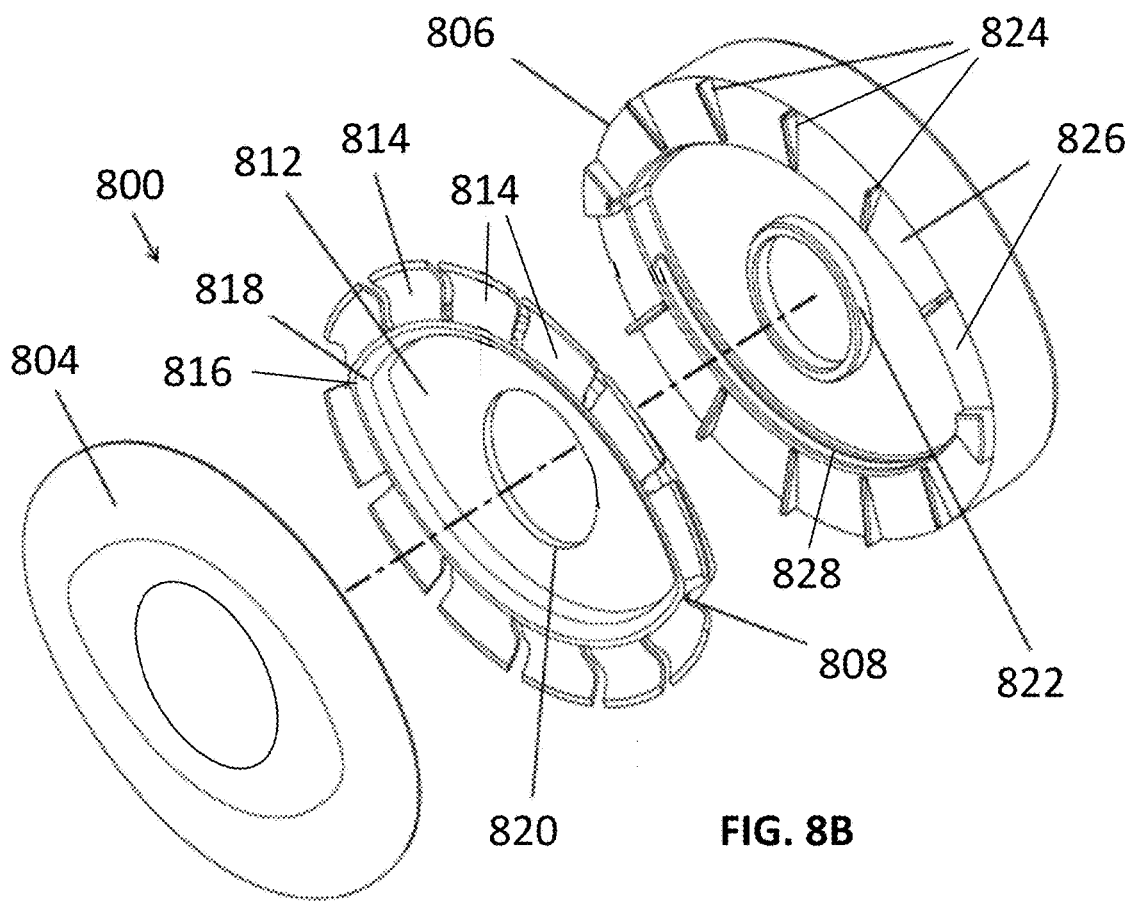
FIG. 8B illustrates an embodiment of a cartridge assembly for storing a lash or lash extension as described herein.

Method 700 may further include, at block 706, optionally retrieving the one or more lash or lash extension before applying the lash or lash extension to the adhesive composition. According to some embodiments, the one or more lash or lash extension may be stored in a container, a cartridge assembly or a combination thereof. For example, the cartridge assembly having the one or more lash or lash extension removably attached thereto may be within a container. A suitable cartridge assembly 800 to which the one or more lash or lash extension may be removably attached is shown in FIGS. 8A and 8B. Cartridge assembly 800 may be configured to hold a plurality of lash extensions 802A-802F (collectively referred to herein as "lash extensions 802"). As shown in FIGS. 8A and 8B, cartridge assembly 800 may include an upper part 804, a lower part 806 and a cartridge 808 therebetween. Upper part 804 may include a protruding member 810 configured to engage with a recess 812 of upper part 804. Protruding member 810 and recess 812 may have an ovular, almond, or eye shape as shown in FIGS. 8A and 8B. A plurality of holding members 814 may extend outwardly, in a radial direction, from an upper edge 816 of a wall 818 surrounding recess 812. Holding members 814 may be spaced apart and configured to receive protruding elements 824 of lower part 806. Cartridge 808 may include an opening 820 configured to receive a respective pass-through member 822 of lower part 806. In some embodiments, opening 820 and pass through member 822 may both be circular as shown in FIGS. 8A and 8B and pass-through member 822 may be configured to at least partially extend into opening 820. In some embodiments, upper part 804 may include a circular member (not shown) configured to engage with pass-through member 822 effectively locking upper part 804 to lower part 806 with cartridge 808 secured therebetween as shown in FIG. 8A.

Protruding elements 824 of lower part 806 may be configured to engage in spaces between holding members 814 as shown in FIGS. 8A and 8B. Holding members 814 of cartridge 808 may be received in spaces defined between protruding members 824 and base walls 826 of lower part 806. Lower part 806 may include a locking mechanism to attach cartridge 808 to lower part 806. The locking mechanism may include a recess 828 configured to receive a corresponding engaging member (not shown) positioned on an outside surface of wall 818. When upper part 804, lower part 806 and cartridge 808 are assembled, as shown in FIG. 8A, the lash extensions 802 may be positioned between holding members 814 and base members 826. Lash extensions 802 may be held in place by the force the holding member 814 against the base members 826. The force is sufficient enough to hold the lash extensions 802 in place during transit, but may be overcome by pulling the las extensions 802 in a radial direction away from cartridge assembly 800.

Figure 9:
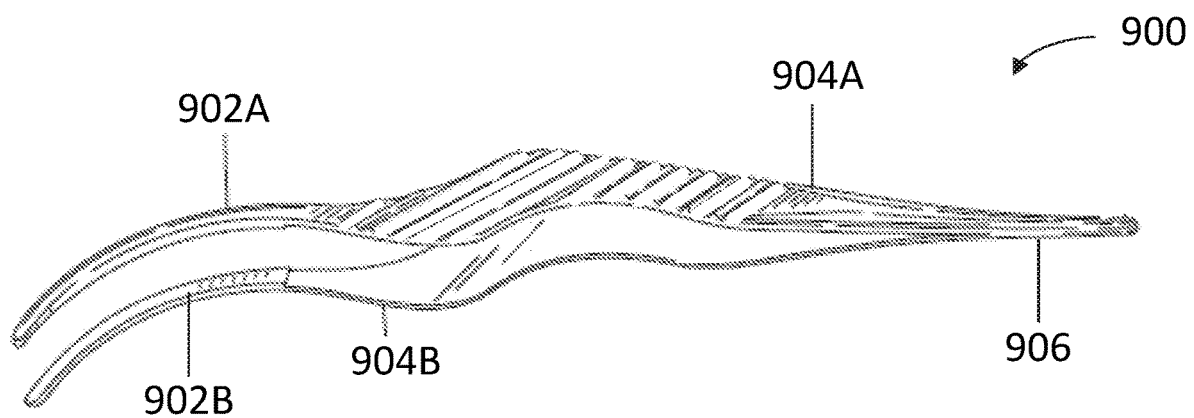
FIG. 9 illustrates an embodiment of a lash applicator for retrieving and applying a lash or lash extension according to embodiments herein.

With reference to method 700, retrieving the one or more lash or lash extension may include removing the one or more lash or lash extension from a container, cartridge assembly 800 or a combination thereof using a lash applicator. Suitable lash applicators include, but are not limited to, a wand, pick, tweezers or a combination thereof. In some embodiments, the one or more lash or lash extension may be retrieved using a lash applicator 900 as shown in FIG. 9. Lash applicator 900 may include tips 902A, 902B configured to move together and apart and to hold one or more lash or lash extension therebetween. Lash applicator 900 may be configured to grip a lash or lash extension from a cartridge and to gently pull free the lash or lash extension. Lash applicator 900 may be used to place the lash or lash extension on the adhesive composition after applied to the surface such as to the underside of a user's natural lashes. Each tip 902A, 902B may be curved such as in the shape of a lash line. In some embodiments, lash applicator 900 includes a first elongate member 904A and a second elongate member 904B. Elongate members 904A, 904B may be attached at end 906. In some embodiments, tips 902A, 902B may be covered by sleeves (also referred to as covers) (not shown) such as plastic sleeves configured to distribute force while applying one or more lash or lash extension to the adhesive composition. Lash applicator 900 may be held following the curve of the eye from the outer corner to the bridge of the nose. Using the curved tips 902A, 902B, the natural lashes with the lash or lash extension positioned thereon may be held between tips 902A, 902B, with or without sleeves thereon, to bond the lash or lash extension together with the natural lashes (e.g., clamp down, bond, hold and release).

At block 708, method 700 may include applying the one or more lash or lash extension to the adhesive composition. The one or more lash or lash extension may be applied to the adhesive composition using lash applicator 900 as described herein. Applying the one or more lash or lash extension can include arranging the lash or lash extension on the adhesive composition such as positioning the lash or lash extension on the adhesive composition on the underside of the natural lashes. Once in place, a lash applicator or other suitable article may be used to apply pressure to the lash or lash extension to adhere it to the adhesive composition. In some embodiments, pressure may be applied for about 10 seconds to about 10 minutes, about 10 seconds to about 5 minutes, or about 30 seconds to about 1 minute.

According to some embodiments, blocks 704, 706 and 708 of method 700 may be independently repeated as needed to retrieve and adhere a plurality of lashes or lash extensions to the surface such as natural lashes. In some embodiments, a plurality of lashes or lash extensions may be arranged on the adhesive composition on the underside of the lashes and once positioned, a lash applicator may be used to apply pressure to the plurality of lashes or lash extensions to bond them to the adhesive composition. In some embodiments, a first set of lashes or lash extensions may be adhered to the underside of the natural lashes and then blocks 704, 706 and 708 of method 700 may be repeated to apply a second set of lashes or lash extension to the bottom side of the first set or to natural lashes along the lash line on the bottom of the eye.

In some embodiments, the method of applying one or more lash or lash extension may include applying another layer of adhesive composition to the one or more lash or lash extension after applying the one or more lash or lash extension. Applying this second layer of adhesive composition to the lash or lash extension already bonded to the natural lashes may increase the wear length of the lash or lash extension. For example, the one or more lash or lash extension may remain bonded to the adhesive composition for at least about 1 day, at least about 5 days, at least about 7 days or at least about 10 days, or up to 10 days, or up to 15 days. Once the second layer of adhesive composition is applied, a lash applicator may be used to apply pressure to the lash or lash extension and the adhesive composition for about 10 seconds to about 10 minutes, about 10 seconds to about 5 minutes, or about 30 seconds to about 1 minute to allow for sufficient drying of the second layer of the adhesive composition.

In some embodiments, method 700 can include one or more of the following acts in addition to, instead of, or in combination with one or more of the above acts (e.g., blocks 702-708). In an act, an adhesive may be applied to the underside of the upper natural lashes, such as the upper natural lashes.

In another act, one or more artificial lash extension from a set of lash extensions may be arranged at the underside of the natural lash. The adhesive may be tacky and cause the artificial lash extensions to adhere to the underside of the natural lash. In some embodiments, the top side of each base of each of the artificial lash extension of the set can be arranged and applied directly to the underside of the natural lashes (rather than to the eyelid). In some embodiments, the one or more artificial lash extension of the set may be arranged to align with the curvature of the lash line. For example, multiple artificial lash extensions may be arranged adjacent to one another (e.g., not overlapping or overlapping) such that the bases align with the curvature of the lash line. Thus, the set of artificial lash extension may become substantially flush with the lash line when the set is arranged proximate to the lash line. In some embodiments, one or more artificial lash extensions can be arranged at the underside of the natural lash at a time. For example, a single artificial lash extension can be arranged first, another artificial lash extension can be arranged subsequently and so forth. In some embodiments, an applicator, as described herein, can be used to arrange the set of artificial lash extensions. The user can further re-arrange one or more of the set of artificial lash extensions as desired.

In another act, one or more of artificial lash extensions may be affixed (e.g., attached or bonded) to the underside of the natural lash. In some embodiments, once the set of artificial lash extensions are arranged in a desired arrangement, the artificial lash extensions can be affixed so that the artificial lash extensions are secured to and more permanently attached (e.g. for days) to a surface, such as the underside of the natural lash. In some embodiments, one or more of an application of pressure or passage of time to cure the adhesive can be used to help affix the set of artificial lash extensions. In some embodiments, an applicator may be used to affix (e.g., apply pressure) the artificial lash extensions to the natural lashes. In some embodiments, the act of arranging and affixing can be combined into a single act.

In some embodiments, the adhesive composition may be used in combination with a lash coating designed to extend (e.g., up to 10 days, or up to 15 days) and refresh the wear of the lash or lash extension. Such lash coating may include water, alcohol, PEG-32, polyvinyl alcohol, glycosyl trehalose, butylene glycol, betaine, hydrogenated starch hydrolysate, glyceryl caprylate, sodium hyaluronate, eriobotrya japonica leaf extract, laminaria japonica extract, artemisia capillaris flower extract, panax ginseng root extract, eugenia caryophyllus (clove) flower extract, acetyl decapeptide-3, soluble collagen, panthenol, biotinoyl tripeptide-1, hydroxyethyl cellulose, acrylates, $C_{10-30}$alkyl acrylate crosspolymer, polyglyceryl-10 laurate, polyurethane-14, amp-acrylates copolymer, specially denatured alcohol 40-B, glycerin, potassium hydroxide, disodium edta, phenoxyethanol, methylparaben and/or combinations thereof.

According to some embodiments, the adhesive composition according to embodiments herein, may be brushed lightly throughout a user's eyelashes. The eyelashes may be brushed out to remove and/or avoid clumps. The adhesive composition may be permitted to dry for about one minute or longer and the adhesive composition may be very tacky after partially drying. The adhesive composition may be permitted to air dry or can be dried using a hot air blower. In some embodiments, a user may apply a second coating of the adhesive composition to the eyelashes on top of the first coat, but may only dab the adhesive composition on the underside of the base of the eyelashes (in the same place a user would begin to apply mascara). The second coating of adhesive composition may be permitted to dry again for at least one (1) minute. A user may then apply artificial lashes to the adhesive composition and a lash applicator to prevent any stickiness. The adhesive composition may be tacky while applying, but dries flat and hard. Adhesive composition that has been applied may be sealed with a sealing composition to remove tackiness. The sealing composition may include acrylates/ethylhexyl, acrylate copolymer, water, alcohol polysorbate 20, phenoxyethanol, hydroxyethylcellulose, ceteareth-25 propylene glycol, PEG-60 hydrogenated castor oil, glycerin, carbon black (black2) and/or combinations thereof. In some embodiments, the sealing composition may include water, alcohol, PEG-32, polyvinyl alcohol, glycosyl trehalose, butylene glycol, betaine, hydrogenated starch hydrolysate, glyceryl caprylate, sodium hyaluronate, eriobotrya japonica leaf extract, laminaria japonica extract, artemisia capillaris flower extract, panax ginseng root extract, eugenia caryophyllus (clove) flower extract, acetyl decapeptide-3, soluble collagen, panthenol, biotinoyl tripeptide-1, hydroxyethylcellulose, acrylates, $C_{10\text{-}30}$alkyl acrylate crosspolymer, polyglyceryl-10 laurate, polyurethane-14, amp-acrylates copolymer, Sd alcohol 40-B, glycerin, potassium hydroxide, disodium EDTA, phenoxyethanol, methylparaben and/or combinations thereof.

The eyelashes and the adhesive composition may be removed after use with a disposable mascara spoolie/brush dipped in an adhesive composition remover. In some embodiments, the adhesive composition remover may include water, cyclopentasiloxane, cyclohexasiloxane, isohexadecane, butylene glycol, sodium citrate, citric acid, benzalkonium chloride, fragrance, disodium edta, poloxamer184, benzyl alcohol, cetrimonium chloride, dipotassium glycyrrhizate, *Oryza sativa* (rice) bran extract, phaseolus radiatus seed extract, citrus aurantium dulcis (orange) fruit extract, *Carica papaya* (papaya) fruit extract, bluel(ci 42090) and/or combinations thereof. The user may slowly brush and scrub through the eyelashes until all of the adhesive composition is removed. A lint-free cotton pad may be used to wipe the eyes.

According to some embodiments, adhesive compositions as described herein may be comprised in any suitable cosmetic composition. Suitable cosmetic compositions include, but are not limited to, mascara, eyeliner, face paint, cream blush, lipstick, foundation, eye shadow. The adhesive composition in such cosmetic compositions may include a colorant to tint the cosmetic composition in any suitable color, for example, black. Such cosmetic compositions may be waterproof. The adhesive composition may be present in the cosmetic composition in an amount of about 0.001 wt % to about 95 wt %, about 0.01 wt % to about 90 wt %, about 0.1 wt % to about 85 wt %, about 1 wt % to about 80 wt %, about 2 wt % to about 75 wt %, about 5 wt % to about 60 wt %, or about 10 wt % to about 50 wt % based on the total weight of the cosmetic composition.

EXAMPLES

Example 1

An illustrative adhesive composition including charcoal was prepared having one or more of water, phenoxyethanol, carbon black, ethylhexyl acrylate and acrylate copolymer and/or charcoal powder. A base was prepared by combining the water, phenoxyethanol and carbon black in a mixing tank for about 1 min to about 30 min. Ethylhexyl acrylate was then added to the base in the mixing tank and the resulting acrylate mixture was further mixed. Subsequently, charcoal powder (e.g., activated charcoal powder) was added to the mixing tank and combined with the other ingredients to form the adhesive composition.

Example 2 (Prophetic)

In another illustrative embodiment, a latex-based adhesive composition may be prepared having the composition set forth in Table 1. In some embodiments, water, phenoxyethanol and carbon black may be combined to form a base to which ethylhexyl acrylate and acrylate copolymer and latex is added and combined to form an acrylate mixture. Charcoal powder may be added to the resulting acrylate mixture to form the latex-based adhesive composition. It should be understood that other methods of preparation and additional and/or alternative ingredients may be utilized.

TABLE 1

Adhesive composition from Example 2.

| Component | Function | % in raw material | % calculated for each substance | Wt % |
|---|---|---|---|---|
| Acrylates/ Ethylhexyl Acrylate Copolymer | Film Former | 100.00 | 100.000 | 0-80 |
| Water | Solvent | 100.00 | 100.000 | 5-80 |
| Carbon Black (Black2) | Colorant | 100.00 | 100.000 | 0-10 |
| Phenoxyethanol | Preservative | 100.00 | 100.000 | 0-3 |
| Charcoal powder | Suspending agent | 100.00 | 100.000 | 0.001-50 |
| Latex | Bonding Agent | 100.00 | 100.000 | 0-80 |

Example 3 (Prophetic)

Solvent-based adhesives may be rubber-solutions and water-based adhesives may be latex-solutions. As such, a wide variety of variations of the ranges may be used in formulating either a solvent-based adhesive or a water-based adhesive with the inclusion of charcoal powder (e.g., activated charcoal powder). Table 2 provides the composition of an illustrative embodiment of an adhesive containing charcoal. The composition may be prepared using the method set forth in Example 2.

TABLE 2

Latex-based adhesive composition from Example 3.

| Component | Function | % in raw material | % calculated for each substance | Wt % |
|---|---|---|---|---|
| Latex | Bonding Agent | 100.00 | 100.000 | 51.50 |
| Water | Solvent | 100.00 | 100.000 | 44.50 |
| Carbon Black (Black2) | Colorant | 100.00 | 100.000 | 3.0 |
| Phenoxyethanol | Preservative | 100.00 | 100.000 | 0.05 |
| Charcoal powder | Suspending agent | 100.00 | 100.000 | 1.0 |

TABLE 3

Latex-based adhesive composition from Example 3.

| Component | Function | % in raw material | % calculated for each substance | Wt % |
|---|---|---|---|---|
| Latex | Bonding Agent | 100.00 | 100.000 | 45.50 |
| Water | Solvent | 100.00 | 100.000 | 50.50 |
| Carbon Black (Black2) | Colorant | 100.00 | 100.000 | 4.0 |
| Phenoxyethanol | Preservative | 100.00 | 100.000 | 0.1 |
| Charcoal powder | Suspending agent | 100.00 | 100.000 | 0.9 |

The foregoing description is not intended to limit the present disclosure to the precise forms or particular fields of use disclosed. As such, it is contemplated that various alternative embodiments and/or modifications to the present disclosure, whether explicitly described or implied herein, are possible in light of the disclosure. Having thus described embodiments of the present disclosure, a person of ordinary skill in the art will recognize that changes may be made in form and detail without departing from the scope of the present disclosure. Thus, the present disclosure is limited only by the claims. Reference to additives in the specification are generally to operative additives unless otherwise noted in the specification.

In the foregoing specification, the disclosure has been described with reference to specific embodiments. However, as one skilled in the art will appreciate, various embodiments disclosed herein can be modified or otherwise implemented in various other ways without departing from the spirit and scope of the disclosure. Accordingly, this description is to be considered as illustrative and is for the purpose of teaching those skilled in the art the manner of making and using various embodiments of the disclosed chemical system. It is to be understood that the forms of disclosure herein shown and described are to be taken as representative embodiments. Equivalent elements, or materials may be substituted for those representatively illustrated and described herein. Moreover, certain features of the disclosure may be utilized independently of the use of other features, all as would be apparent to one skilled in the art after having the benefit of this description of the disclosure. Expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural.

As used herein, the singular forms "a," "an," and "the" include plural references unless the context clearly indicates otherwise. Thus, for example, reference to "an active ingredient" includes a single active ingredient as well as a mixture of two or more different active ingredients. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances.

As used herein, the term "about" in connection with a measured quantity, refers to the normal variations in that measured quantity as expected by one of ordinary skill in the art in making the measurement and exercising a level of care commensurate with the objective of measurement and the precision of the measuring equipment. In certain embodiments, the term "about" includes the recited number ±10%, such that "about 10" would include from 9 to 11.

The term "at least about" in connection with a measured quantity refers to the normal variations in the measured quantity, as expected by one of ordinary skill in the art in making the measurement and exercising a level of care commensurate with the objective of measurement and precisions of the measuring equipment and any quantities higher than that. In certain embodiments, the term "at least about" includes the recited number minus 10% and any quantity that is higher such that "at least about 10" would include 9 and anything greater than 9. This term can also be expressed as "about 10 or more." Similarly, the term "less than about" typically includes the recited number plus 10% and any quantity that is lower such that "less than about 10" would include 11 and anything less than 11. This term can also be expressed as "about 10 or less."

Unless otherwise indicated, all parts and percentages are by weight. Weight percent (wt. %), if not otherwise indicated, is based on an entire composition free of any volatiles, that is, based on dry solids content.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Further, various embodiments disclosed herein are to be taken in the illustrative and explanatory sense, and should in no way be construed as limiting of the present disclosure. All joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed broadly.

Moreover, such joinder references do not necessarily infer that two elements are directly connected to each other.

Additionally, all numerical terms, such as, but not limited to, "first", "second", "third", "primary", "secondary", "main" or any other ordinary and/or numerical terms, should also be taken only as identifiers, to assist the reader's understanding of the various elements, embodiments, variations and/or modifications of the present disclosure, and may not create any limitations, particularly as to the order, or preference, of any element, embodiment, variation and/or modification relative to, or over, another element, embodiment, variation and/or modification.

It will also be appreciated that one or more of the elements depicted in the drawings/figures can also be implemented in a more separated or integrated manner, or even removed or rendered as inoperable in certain cases, as is useful in accordance with a particular application.

What is claimed is:

1. An adhesive composition for application of one or more beauty articles, comprising:
    an acrylate component in an amount of about 10 percent by weight (wt %) to about 55 wt % based on a total weight of the adhesive composition;
    a charcoal component comprising at least one of activated charcoal, acid washed activated charcoal, high purity activated charcoal, impregnated charcoal, pharmaceutical grade activated charcoal, acid-washed granular activated charcoal made from coconut shell or combinations thereof; and
    a preservative in an amount of about 0.01 wt % to about 1.0 wt %,
    wherein the preservative comprises phenoxyethanol and the acrylate component comprises an acrylate/ethylhexyl acrylate copolymer.

2. The adhesive composition of claim 1, wherein the acrylate component comprises at least one of acrylates, polyacrylates, acrylamide polymers, alkyl acrylates, (meth)acrylates, acrylic acids, (meth)acrylic acid, acrylamide, (meth)acrylamide polymers, polymethacrylate, polymethylmethacrylate, $C_{1-6}$hydroxyalkyl (meth)acrylates, $C_{1-6}$alkoxy $C_{1-6}$alkyl (meth)acrylates, polyoxyalkylene (meth)acrylates, $C_{1-6}$alkylpolyoxyalkylene (meth)acrylates, $C_{8-22}$alkyl (meth)acrylates, methyl(meth)acrylate, ethyl(meth)acrylate, propyl(meth)acrylate, butyl(meth)acrylate, isobutyl(meth)acrylate, pentyl(meth)acrylate, hexyl(meth)acrylate, 2-hydroxyethyl(meth)acrylate, 2-methoxyethyl(meth)acrylate, polyethyleneglycol (meth)acrylate, polyethyleneglycol methyl ether (meth)acrylate, polyethyleneglycol ethyl ether (meth)acrylate, octyl(meth)acrylate, 2-ethylhexyl(meth)acrylate, lauryl(meth)acrylate, stearyl(meth)acrylate, 2-ethylhexyl acrylate, copolymers thereof, quaternary salts thereof, ethylhexyl acrylate copolymer, ethylhexyl acrylate and acrylate copolymer, acrylate/ammonium methacrylate copolymer, acrylate/$C_{12-22}$alkylmethacrylate copolymer, styrene/acrylate copolymer, acrylamide/acryloyldimethyltaurate copolymer, potassium acrylate/$C_{10-30}$alkyl acrylate crosspolymer, sodium acrylate/$C_{10-30}$alkyl acrylate crosspolymer, aminomethylpropanol-acrylate copolymer, glyceryl acrylate/acrylic acid copolymer, hydroxyethylacrylate/sodium acryloyldimethyl tau rate copolymer, sodium hydroxyethylacrylate/acryloyldimethyl taurate copolymer, styrene/acrylates/ammonium methacrylate copolymer, sodium polyacrylate, sodium polyacrylate starches, polyglyceryl methacrylates, ammonium acryloyldimethyltaurate/VP copolymer or combinations thereof.

3. The adhesive composition of claim 1, wherein the charcoal component comprises at least one of a carbonaceous material derived from wood, bamboo, hardwood, peat, coal, coke, petroleum, bones, coconut shells, nutshells, coir, lignite or combinations thereof.

4. The adhesive composition of claim 1, comprising the charcoal component in an amount of about 0.001 wt % to about 5 wt % based on a total weight of the adhesive composition.

5. The adhesive composition of claim 1, wherein the charcoal component comprises a plurality of units comprising at least one of powder, particles, granules, extrudates, pellets or combinations thereof.

6. The adhesive composition of claim 1, wherein the charcoal component comprises a plurality of units comprising a size of less than about 1 mm or comprising a mean size of about 1 mm.

7. The adhesive composition of claim 1, further comprising water in an amount of about 1 wt % to about 90 wt % based on a total weight of the adhesive composition.

8. The adhesive composition of claim 1, further comprising a colorant, wherein the colorant comprises at least one of carbon black, azo dye, quinophthalone dye, triphenylmethane dye, xanthene dye, iron oxide, iron hydroxide, titanium dioxide, sunset yellow dye, allura red dye, amaranth dye, koki neil red dye, azogeranin dye, tartrazine dye, brilliant black dye, canthaxanthin dye, patent blue dye, fast green dye, brilliant blue dye, acid green dye, erythrosine dye, quinoline yellow, indigotin, curcumin or combinations thereof.

9. The adhesive composition of claim 1, wherein the preservative comprises at least one of phenoxyethanol, benzalkonium chloride, sodium dehydroacetate, benzyl alcohol, phenethyl alcohol, esters of p-hydroxybenzoic acid, imidazolidinyl urea, diazolidinyl urea, carboxylic acids or combinations thereof.

10. The adhesive composition of claim 1, wherein the adhesive composition is free of a cyanoacrylate, latex, a formaldehyde or any combination thereof.

11. The adhesive composition of claim 1, comprising a viscosity of about 10,000 cP to about 50,000 cP at 25° C.

12. The adhesive composition of claim 1, comprising an adhesive strength of about 0.5 MPa to about 100 MPa.

13. An adhesive composition for application of one or more beauty articles, comprising:
    an acrylate component in an amount of about 45 percent by weight (wt %) to about 55 wt % based on a total weight of the adhesive composition;
    a charcoal component in an amount of about 0.001 wt % to about 2 wt %, wherein the charcoal component comprises at least one of activated charcoal, acid washed activated charcoal, high purity activated charcoal, impregnated charcoal, pharmaceutical grade activated charcoal, acid-washed granular activated charcoal made from coconut shell or combinations thereof;
    a preservative in an amount of about 0.01 wt % to about 1.0 wt %; water in an amount of about 40 wt % to about 50 wt %; and
    a colorant in an amount of about 1 wt % to about 4 wt %.

* * * * *